(12) United States Patent
Mitsuhashi et al.

(10) Patent No.: US 9,150,920 B2
(45) Date of Patent: Oct. 6, 2015

(54) METHODS OF CHARACTERIZING HOST RESPONSIVENESS TO INTERFERON BY EX VIVO INDUCTION OF INTERFERON-RESPONSIVE MARKERS

(75) Inventors: Masato Mitsuhashi, Irvine, CA (US); Ernest C. Borden, Cleveland, OH (US)

(73) Assignees: HITACHI CHEMICAL CO., LTD., Tokyo (JP); HITACHI CHEMICAL COMPANY AMERICA, LTD, Cupertino, CA (US); THE CLEVELAND CLINIC FOUNDATION, Cleveland, OH (US)

( * ) Notice: Subject to any disclaimer, the term of this patent is extended or adjusted under 35 U.S.C. 154(b) by 39 days.

(21) Appl. No.: 13/695,755

(22) PCT Filed: May 3, 2011

(86) PCT No.: PCT/US2011/035045
§ 371 (c)(1),
(2), (4) Date: Nov. 1, 2012

(87) PCT Pub. No.: WO2011/140125
PCT Pub. Date: Nov. 10, 2011

(65) Prior Publication Data
US 2013/0084577 A1  Apr. 4, 2013

Related U.S. Application Data

(60) Provisional application No. 61/332,677, filed on May 7, 2010, provisional application No. 61/387,668, filed on Sep. 29, 2010.

(51) Int. Cl.
*C12Q 1/68* (2006.01)
*C12Q 1/70* (2006.01)

(52) U.S. Cl.
CPC ............ *C12Q 1/6876* (2013.01); *C12Q 1/6883* (2013.01); *C12Q 1/6886* (2013.01); *C12Q 2600/106* (2013.01); *C12Q 2600/158* (2013.01)

(58) Field of Classification Search
CPC ..... C12Q 1/6876; C12Q 1/6886; C12Q 1/706
See application file for complete search history.

(56) References Cited

U.S. PATENT DOCUMENTS

| 2004/0170961 A1* | 9/2004 | Meritet et al. ............... 435/5 |
| 2006/0008807 A1 | 1/2006 | O'Hara et al. |
| 2006/0198787 A1 | 9/2006 | Blatt |
| 2007/0292448 A1 | 12/2007 | Lebkowski et al. |
| 2008/0206761 A1 | 8/2008 | Mitsuhashi |
| 2009/0011410 A1 | 1/2009 | Mitsuhashi |
| 2009/0111128 A1 | 4/2009 | Mitsuhashi |
| 2009/0136447 A1 | 5/2009 | Cannon et al. |
| 2009/0203064 A1 | 8/2009 | Ericson |
| 2009/0215064 A1 | 8/2009 | Mitsuhashi et al. |
| 2012/0258076 A1 | 10/2012 | Mitsuhashi |
| 2014/0147470 A1 | 5/2014 | Mitsuhashi |

FOREIGN PATENT DOCUMENTS

| JP | 2009/178057 | 8/2009 |
| WO | 00/35473 | 6/2000 |
| WO | 00/52209 | 9/2000 |
| WO | WO 2008/095907 | 8/2008 |

OTHER PUBLICATIONS

Peng et al. Independent and cooperative antiviral actions of beta interferon and gamma interferon against herpes simplex virus replication in primary human fibroblasts. J. Virology (2008) vol. 82, No. 4, pp. 1934-1945.*
Sixtos-Alonso et al., IFN-stimulated Gene Expression is a Useful Potential Molecular Marker of Response to Antiviral Treatment with Peg-IFNalpha 2b and Ribavirin in Patients with Hepatitis C Virus Genotype 1, Arch. Med. Res., vol. 42(1):28-33 (2011).
Baechler et al., Interferon-inducible Gene Expression Signature in Peripheral Blood Cells of Patients with Severe Lupus, PNAS, vol. 100(5):2610-2615 (2003).
Mitsuhashi, Masato. Ex vivo simulation of leukocyte function: Stimulation of specific subset of leukocytes in whole blood followed by the measurement of function-associated mRNAs. Journal of Immunological Methods 363 (2010) 95-100.
International Search Report and Written Opinion of the International Searching Authority for International Application No. PCT/US12/47240 dated Oct. 4, 2012.
European Search Report for International Application No. PCT/US2010/059552 dated Nov. 4, 2013.
Ahmadzadeh et al., "IL-2 administration increases CD4+CD25hi Foxp3+ regulartory T cells in cancer paitents," Blood, 2006, vol. 107, pp. 2409-2414.
Benner et al., "Evolution, language and analogy in functional genomics," Trends in Genetics, vol. 17, No. 7, pp. 414-418.
Cheung et al., Natural variation in human gene expression assessed in lymphoblastoid cells, Nature Genetics, 2003, vol. 33, pp. 422-425.
Dannull et al., "Enhancement of vaccine-mediated antitumor immunity in cancer paitents after depletion of regulartory T cells," J. Clin. Invest 2005, vol. 115, No. 12, pp. 3623-3633.
Freezor, et al. Genomic and Proteomic Determinants of Outcome in Patients Undergoing Thoracoabdominal Aortic Aneurysm Repair. The Journal of Immunology 2004, 172: 7103-7109.
Gavin, "Single-cell analysis of normal and FOXP3-mutant human T cells: FOXP3 expression without regulatory T cell development," Proceedings National Academy of Sciences, 2006, vol. 103, No. 17, pp. 6659-6664.
Moriconi, et al. Quantitative gene expression of cytokines in peripheral blood Leukocytes stimulated in vitro: modulation by the antitumor necrosis factor-alpha antibody infliximab and comparison with the mucosal cytokine expression in patients with ulcerative colitis. Translational Research 2007, 150:223-232.

(Continued)

*Primary Examiner* — Gary Benzion
*Assistant Examiner* — David Thomas
(74) *Attorney, Agent, or Firm* — Knobbe Martens Olson & Bear, LLP

(57) ABSTRACT

Embodiments of the invention relate generally to ex vivo methods of quantifying expression of interferon responsive genes and characterizing an individual's potential responsiveness to interferon administration. Certain embodiments relate to methods to monitor the efficacy of ongoing interferon therapy by evaluating expression of interferon responsive genes before and after interferon administration.

12 Claims, 33 Drawing Sheets

(56) References Cited

OTHER PUBLICATIONS

Newton et al., "On Differential Variability of Expression Ratios: Improving Statistical Inference about Gene Expression Changes from Microarray Data," Journal of Computational Biology, 2001, vol. 8, No. 1, pp. 37-52.
Pons et al., "FoxP3 in Peripheral Blood is Associated With Operational Tolerance in Liver Transplant Patients During Immunosuppression Withdrawal," Clinical Transplantation, 2008, vol. 86, No. 10, pp. 1370-1378.
Powell, et al., Inability to Mediate Prolonged Reduction of Regulatory T Cells After Transfer of Autologous CD25- depleted PBMC and Interleukin-@ AFter Lymophodepleting Chemotherapy, J. Immunotherapy, vol. 30(4): 438-447 (May/Jun. 2007).
Powrie. Immune Regulation in the Intestine. A Balancing Act between Effector and Regulatory T Cell Responses. Ann. N.Y. Acad. Sci. 1029: 132-141 (2004).
Sakaguchi, "Naturally arising Foxp3-expressing CD25+ CD4+ regulatory T cells in immunological tolerance to self and non-self," Nature Immunology, 2006, vol. 6, No. 4, pp. 345-352.
Wu, "Analysing gene expression data from DNA microarrays to identify candidate genes," Journal of Pathology, 2001, vol. 195, pp. 53-65.
Zorn, et al., "IL-2 regulates FOXP3 expression in human CD4+CD25+ regulatory T cells through a STAT-dependent mechanism and induces the expansion of these cells in vivo," Blood, 2006, vol. 108, pp. 1571-1579.
European Extended Search Report, Re EPO Application No. 10842460.7, dated Nov. 4, 2013.
Japanese Office Action, re JP Application No. 2013-510164, mailed Aug. 19, 2014.
Apr. 30, 2015 Final Office Action for Japanese Patent Application No. 2013-510164 (PCT/US2011/305045).
Medical Clinics of Japan, Aug. 2004, vol. 30 (5pgs.).
Biomedicine & Therapeutics, vol. 38 No. 9, Sep. 2004 (8 pages).
"A low-density cDNA microarray with a unique reference RNA: pattern recognition analysis for IFN efficacy prediction to HCV as a model", Daiba et al., Biochemical and Biophysical Research Communiations 315 (2004) pp. 1088-1096.
Assessment of the Effect of Recombinant IL-3 by the Serum-Free Liquid Culture Method, Isoyama et el., pp. 201-205, Department of Pediatrics, Showa University Fujigaka Hospital, 1992.

* cited by examiner

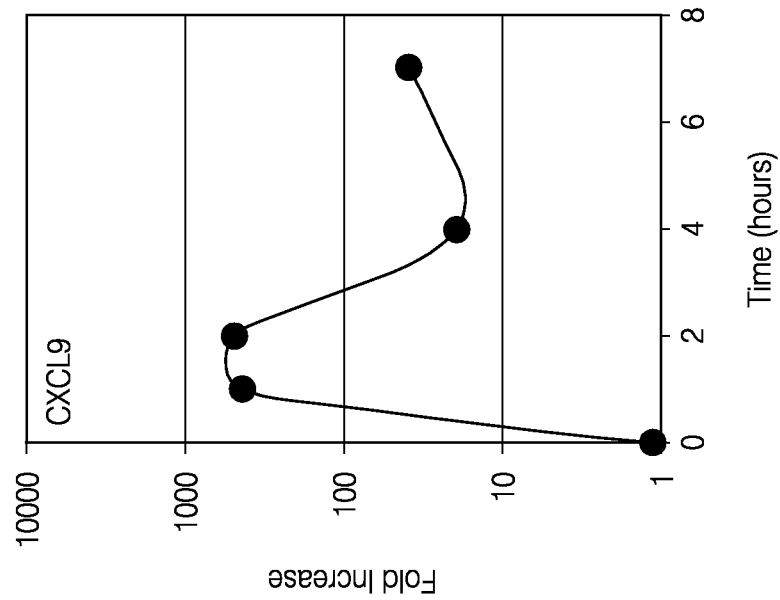
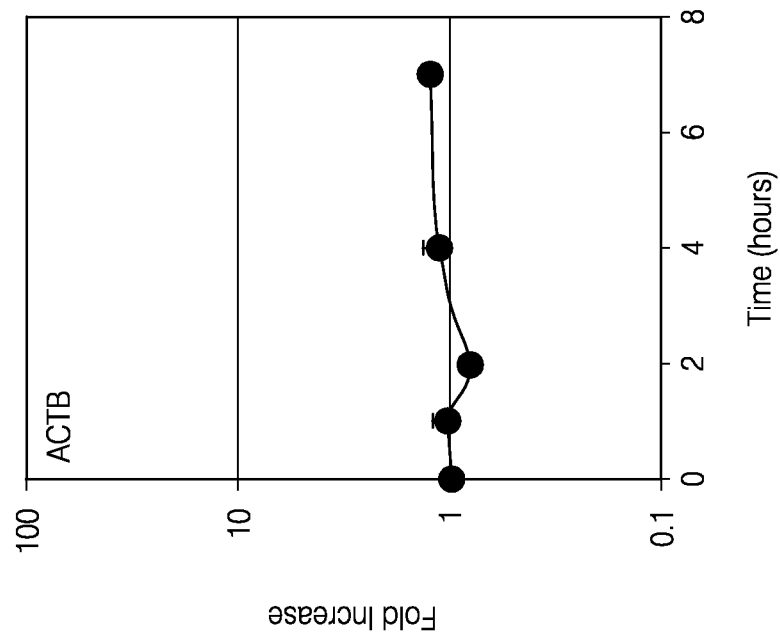
FIG. 4B
FIG. 4A

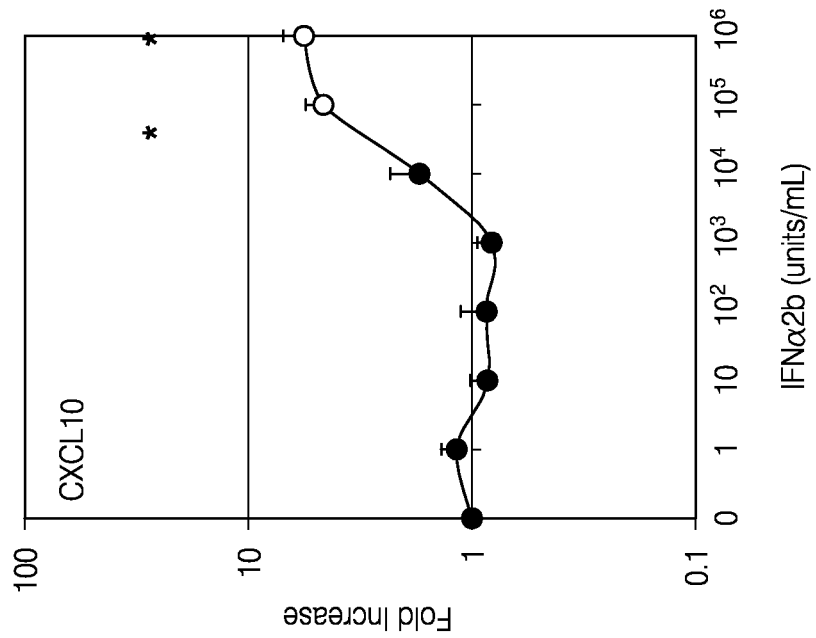
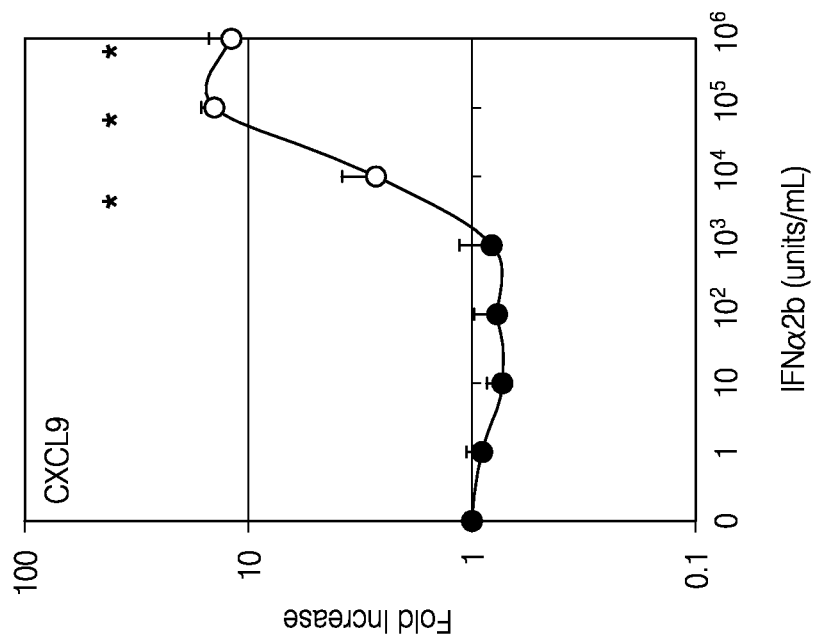
FIG. 9B
FIG. 9A

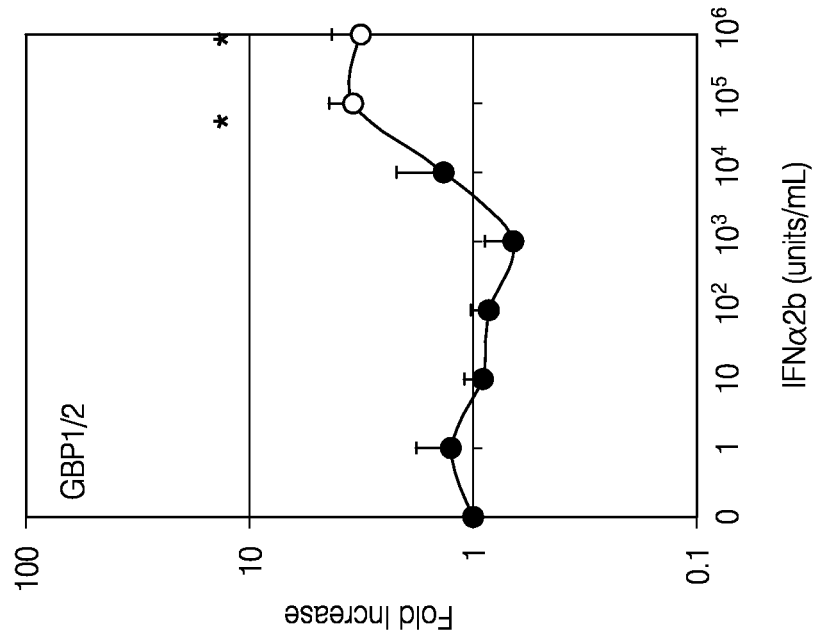
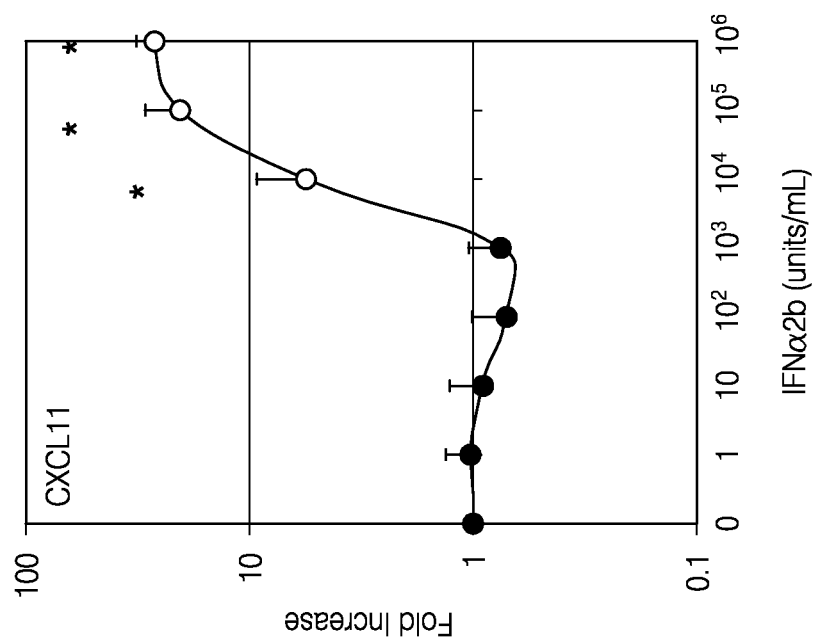

Sustained increase > 1 day (no exception)

Sustained increase > 1 day (with exception)

Sustained increase > 1 day (with exception)

Transient increase < 1 day

US 9,150,920 B2

METHODS OF CHARACTERIZING HOST RESPONSIVENESS TO INTERFERON BY EX VIVO INDUCTION OF INTERFERON-RESPONSIVE MARKERS

RELATED CASES

The contents of each priority document listed in the accompanying Application Data Sheet is incorporated in its entirety by reference herein. This application also incorporates by reference the sequence listing submitted as ASCII text filed via EFS-Web on Aug. 29, 2012. The Sequence Listing is provided as a filed entitled "ST25 Sequence Listing—HITACHI.098NP", created on Nov. 8, 2012 and which is 28.1 kilobytes in size.

BACKGROUND

1. Field of the Invention

Embodiments of the present invention relate generally to methods for the characterization of the responsiveness of an individual to certain therapeutic agents. More specifically, embodiments disclosed herein relate to the prediction of the whether an individual will respond or fail to respond to interferon (IFN) therapy in certain disease contexts, including cancer and/or hepatitis therapy. Certain embodiments relate to methods of monitoring the effectiveness of ongoing IFN therapy in an individual.

2. Description of the Related Art

Interferons are anti-viral drugs used in laboratory research settings, as well as clinically, to combat viral infections and/or in therapies for indications such as cancer. It is clinically approved for treatment of hepatitis B and C as well as a variety of cancers, including certain leukemias, myelomas, and melanomas.

Hepatitis is a viral liver disease characterized by the presence of inflammatory cells in the liver. While there are many causes of the disease (including exposure to infectious blood or body fluids, unprotected sexual contact, blood transfusions, use of contaminated needles, and vertical transmission from mother to child during childbirth), diagnosis is challenging because viral antigens may not appear until well after initiation of the infection. Hepatitis also exists in many forms, most prominently Hepatitis B (caused by the hepatitis B virus, "HBV") and Hepatitis C (caused by the hepatitis C virus "HCV"). Both of these forms of Hepatitis may either be acute (less than six months to resolution) or chronic (infection greater than six months).

Both HBV and HCV exist in various genetic subtypes, which affect the severity of the disease symptoms, the likelihood of complications, and the possible responsiveness of the host to various available treatments, of which interferon therapy one.

IFN has anti-proliferative, pro-apoptotic, and anti-angiogenic effects on cultured cancer cells, but the particular molecular targets and mechanisms triggered by exogenous IFN remain under investigation. Moreover, the variety of etiologies that underlie cancers may limit the efficacy of a single therapeutic agent or regime against more than a few related types of cancer.

Despite its current clinical use, there remains a need for assessing the likelihood that a given individual will respond positively to IFN administration. There is also a need for monitoring the ongoing efficacy of IFN administration in an individual receiving the IFN on an ongoing basis.

SUMMARY

In several embodiments, there is provided an ex vivo method for characterizing the potential responsiveness of an individual to administration of interferon comprising exposing a first sample of whole blood from the individual to interferon in a solvent for an amount of time sufficient for the interferon to alter the expression of one or more interferon-responsive markers, exposing a second sample of whole blood from the individual to the solvent without the interferon (for the same amount of time), quantifying the effect of said interferon as a change in expression of the one or more interferon-responsive markers by measuring the amount of mRNA encoding one or more of the interferon-responsive markers in both the first and second whole blood samples, comparing the quantified effect of interferon on expression of one or more of the interferon-responsive markers with a normal effect of interferon on expression of one or more of the interferon responsive markers, wherein the normal effect is calculated as an average of change in expression levels of a panel of control individuals, characterizing the potential responsiveness of the individual by identifying significant differences between the change in expression of one or more of the interferon-responsive markers in the individual and the average change in expression of one or more of the interferon-responsive markers in the panel of control individuals. The individual is potentially responsive to interferon if the change in expression in the individual is substantially greater than the change in the panel of control individuals, and the individual is potentially non-responsive to interferon if the change in expression in the individual is substantially less than the change in the panel of control individuals. In several embodiments, one or more of the interferon-responsive markers comprises a marker that increases in response to interferon. In several embodiments, one or more of the interferon-responsive markers comprises a marker that decreases in response to interferon.

The potential responsiveness of the individual is characterized by identifying significant differences between the expression of the one or more interferon-responsive markers in the first whole blood sample and the expression of the one or more interferon-responsive markers in the second whole blood sample. The individual is potentially responsive to interferon if the amount of one or more mRNA encoding an interferon-responsive marker from the first blood sample is significantly increased as compared to the amount mRNA encoding the same interferon-responsive marker in the second blood sample. The individual is potentially non-responsive to interferon if the amount of one or more mRNA encoding an interferon-responsive marker from the first blood sample is significantly decreased as compared to the amount of mRNA encoding the same interferon-responsive marker in the second blood sample.

In several embodiments, provided herein is a method for determining the efficacy of interferon therapy in an individual comprising obtaining a first sample of whole blood from the individual prior to interferon administration, obtaining a second sample of whole blood from the individual after interferon administration, quantifying the expression of one or more interferon-responsive markers by measuring the amount of mRNA encoding the one or more interferon-responsive markers in both the first whole blood sample and the second whole blood sample; and determining the efficacy of interferon therapy by comparing the expression of the one or more interferon-responsive markers in the first whole blood sample and in the second whole blood sample.

In several embodiments interferon therapy is determined to be effective if the expression of one or more of the interferon-responsive markers is significantly different in the second blood sample as compared to the first blood sample. In several embodiments interferon therapy is not effective if the expression of one or more of the interferon-responsive markers does not differ between the second blood sample as compared to the first blood sample.

In several embodiments the one or more interferon-responsive markers are selected from the group consisting of CCL8, CXCL9, CXCL10, CXCL11, GBP, XAF1, SOCS1, G1P2, BST2, IRF7, TNFSF5, IL8, IL23, TNFSF10, TNFRSF5, TNFSF6, TNFSF8, TNFSF15, CCL20, CXCL1, CXCL2, CXCL3, CXCL5, IL1B, IFN gamma, VEGF, ISG15, STAT1, ICOS, and AIM2.

In several embodiments, the interferon is chosen from the group consisting of a type I interferon, a type II interferon, and a type III interferon. In some embodiments, the interferon is chosen from the group consisting of interferon alpha, interferon beta, interferon omega, interferon gamma, combinations thereof, and subtypes thereof. In some embodiments the interferon is interferon alpha 2b. In some embodiments, the interferon alpha 2b is present in a concentration from about 1 to about 100,000 units per mL. In some embodiments, the interferon alpha 2b is present in a concentration of about 5,000 units per mL to about 15,000 units per mL. In several embodiments, the interferon alpha 2b is administered to treat a viral infection. In several embodiments, the viral infection is caused by a hepatitis virus. In other embodiments, the interferon alpha 2b is administered as an anti-cancer therapy.

In several embodiments, the solvent is phosphate buffered saline or other similar relatively inert physiologic substance (e.g., normal saline or distilled water). In several embodiments the exposing of the samples to the interferon or solvent is for a time between one hour and seven hours. In one embodiment the exposing is for four hours. In several embodiments, the exposure occurs at about thirty-seven (37) degrees Celsius.

In several embodiments the whole blood is obtained from a mammal and in several embodiments the whole blood is heparinized. In some embodiments the mammal is a human. In some embodiments, the first and second samples are obtained from an individual having one or more of hepatitis, an autoimmune disorder, or cancer and in need of treatment therefore.

Also provided for herein is a method for preparing a device for quantification of mRNA encoding one or more interferon-responsive markers in whole blood samples comprising, obtaining a first sample and a second sample of whole blood, stimulating leukocytes in the first sample with a stimulating agent in a solvent, exposing leukocytes in the second sample with the solvent in the absence of stimulating agent, adding each of the first and second samples to a filter plate, removing erythrocytes and blood components other than leukocytes from each of the first and second samples by filtration to yield leukocytes from each of the first and second samples on the filter plate, lysing the leukocytes from each of the first and second samples on the filter plate using a lysis buffer that comprises at least one reverse primer for a marker encoding an interferon-responsive marker to produce a first lysate comprising the primer and mRNA from the first sample and a second lysate comprising the primer and mRNA from the second sample, wherein the primer hybridizes to mRNA encoding an interferon-responsive marker present in the samples, and transferring the first and second lysates to an oligo (dT)-immobilized plate to capture the mRNA from both the first and second samples, including mRNA to which the primer has bound.

BRIEF DESCRIPTION OF THE FIGURES

FIGS. 4A-4H. Fold change relationship between various mRNA expression and IFNα-2b stimulation. Data shown in FIG. 3 transformed into Fold Increase values. Each data point represents mean±s.d. (n=9).

FIGS. 7A-7D. Ex vivo assay procedure.

FIGS. 9A-9H. Ex vivo dose response relation of various mRNA to IFNα-2b stimulation.

DETAILED DESCRIPTION

Figure 1:
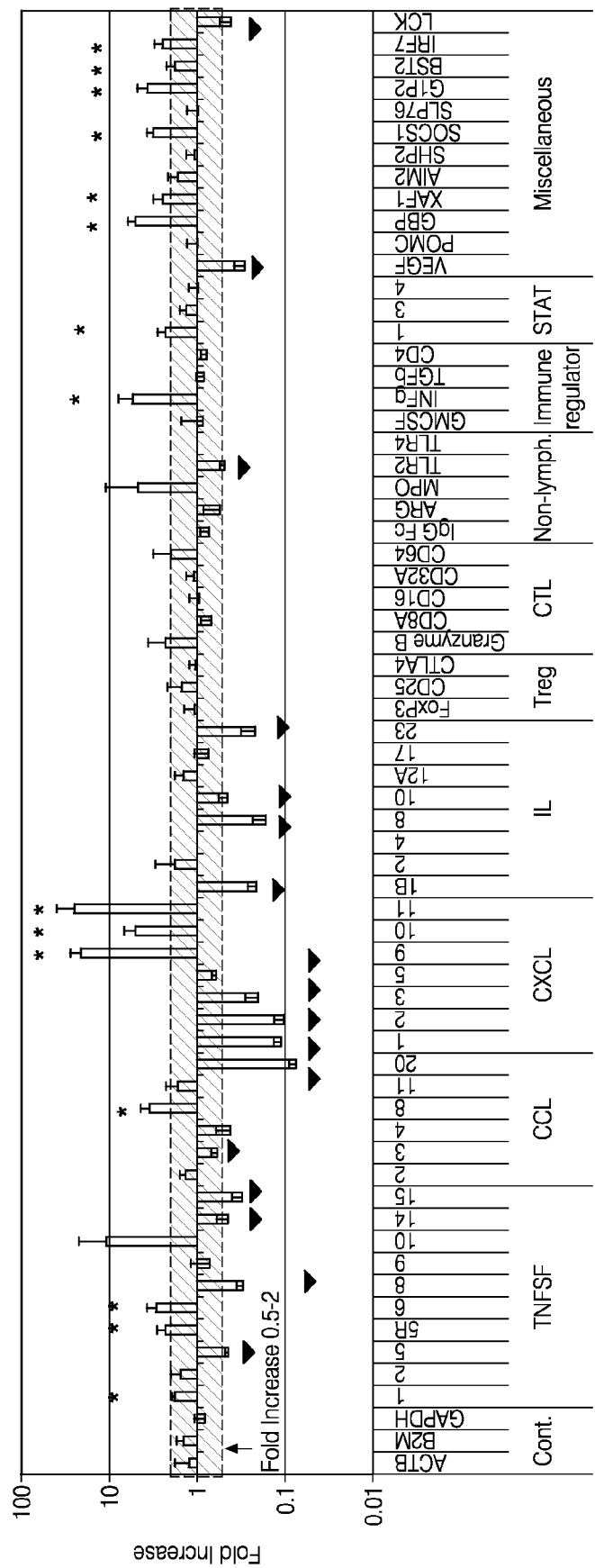
FIG. 1. Ex vivo screening of various mRNA species for responsiveness to stimulation by IFNα-2b. Each bar represents mean±s.d. (n=9). Significant increases are denoted by a "*" and significant decreases by a "▼". Blanket: fold increase between 0.5 and 2.
Figure 2B:
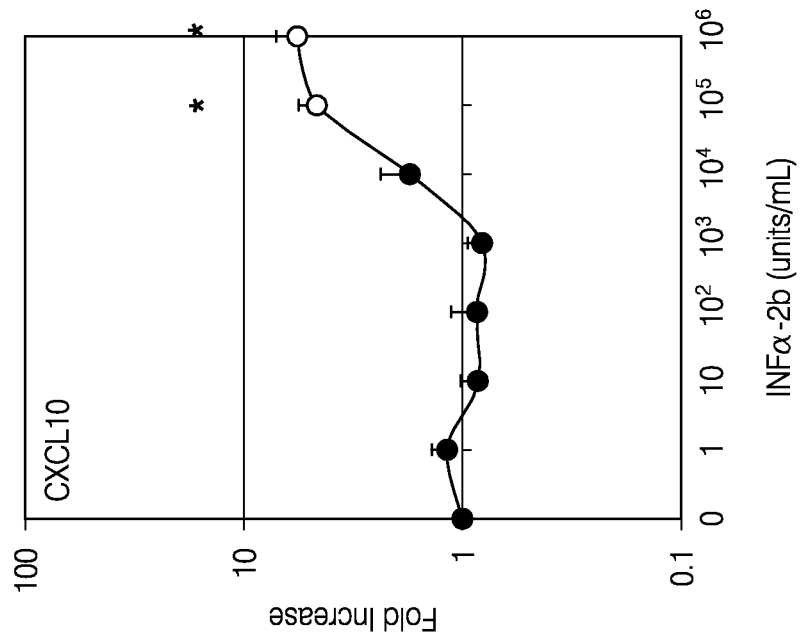
FIGS. 2A-2H. Ex vivo dose response relation of various mRNA to IFNα-2b stimulation. Each data point represents mean±s.d. (n=9). Significant increases are denoted by a "*" and significant decreases by a "▼".
Figure 2A:
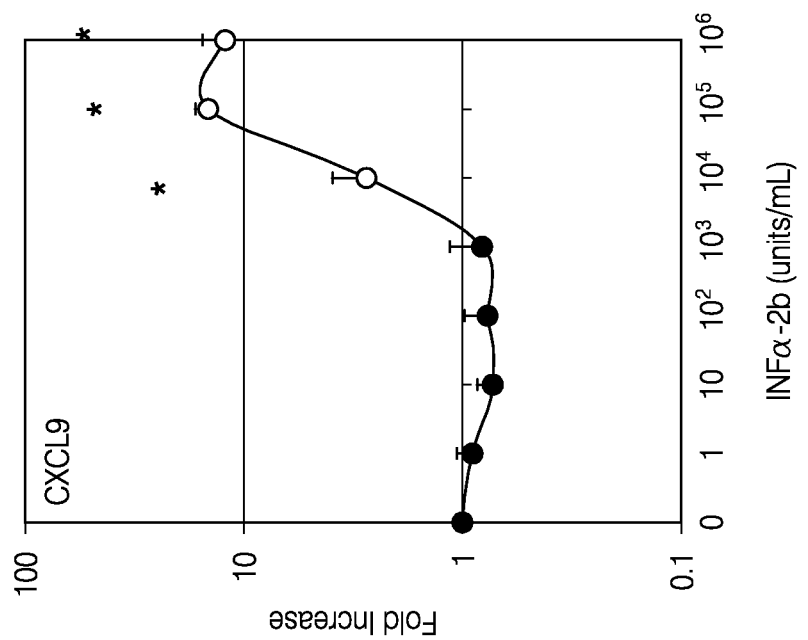
Figure 2D:
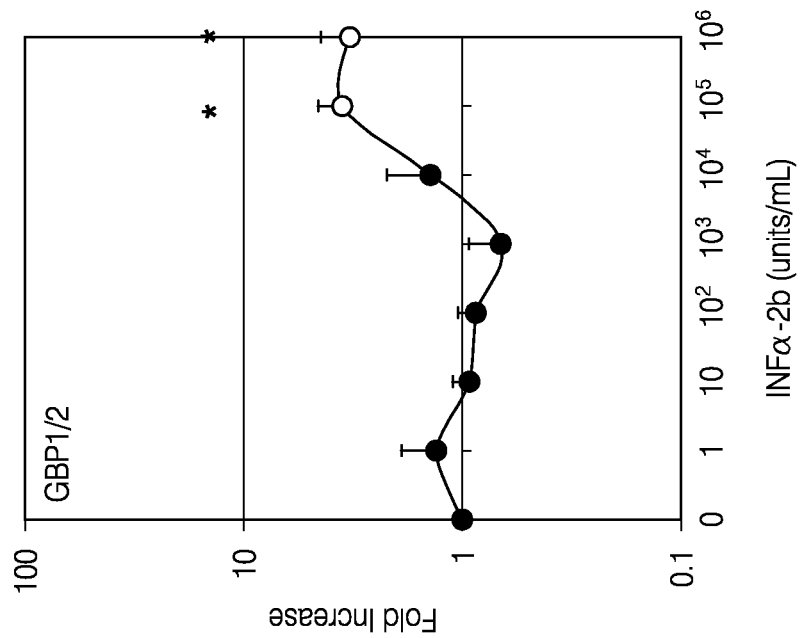
Figure 2C:
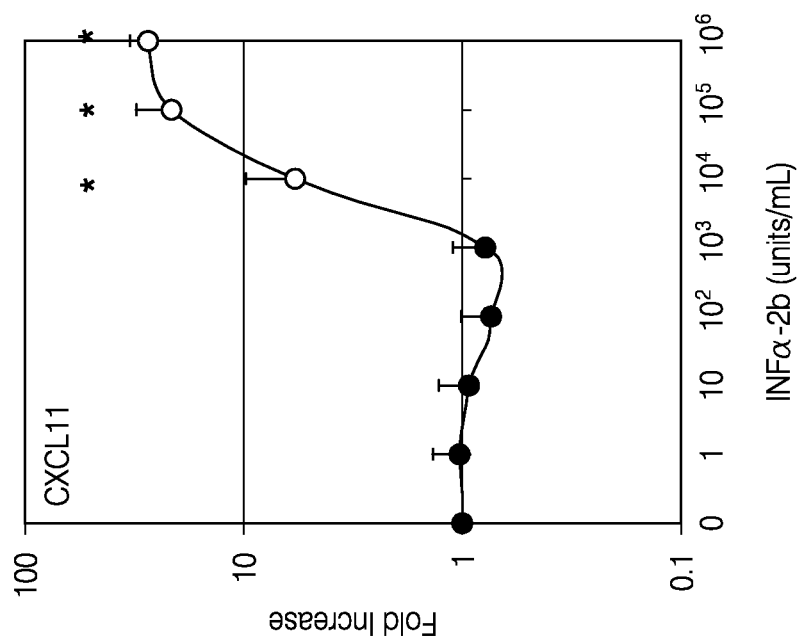
Figure 2F:
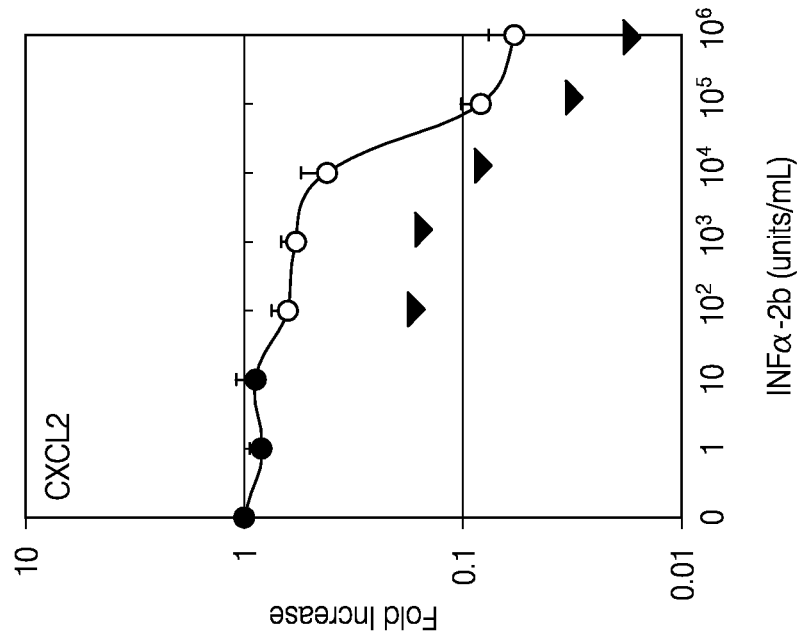
Figure 2E:
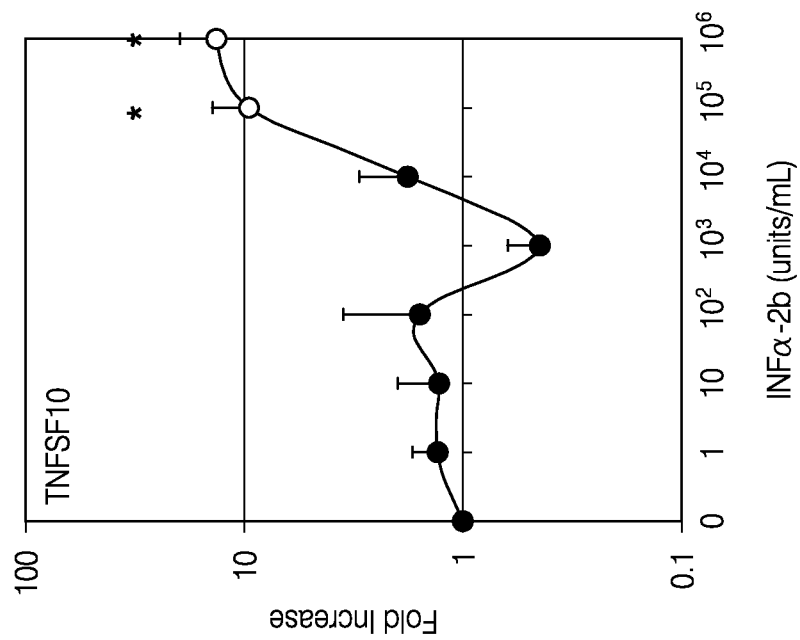
Figure 2H:
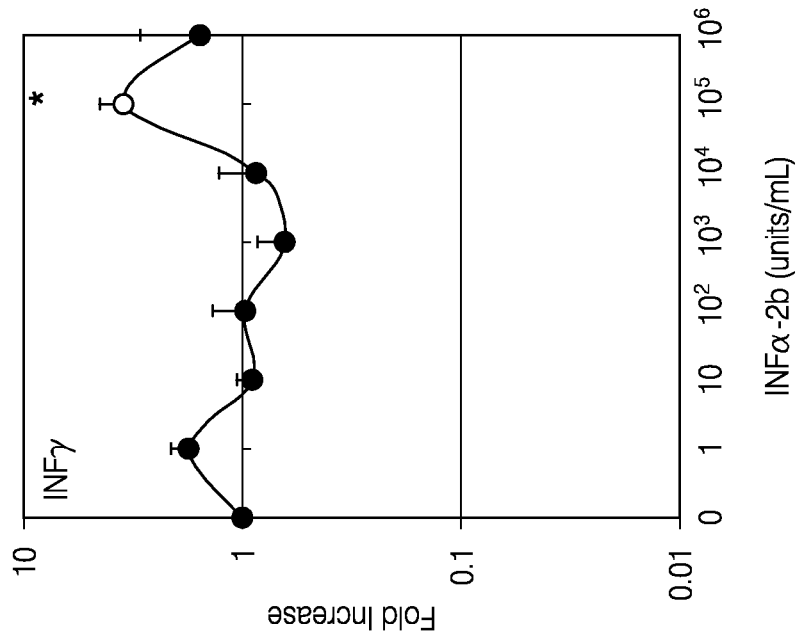
Figure 2G:
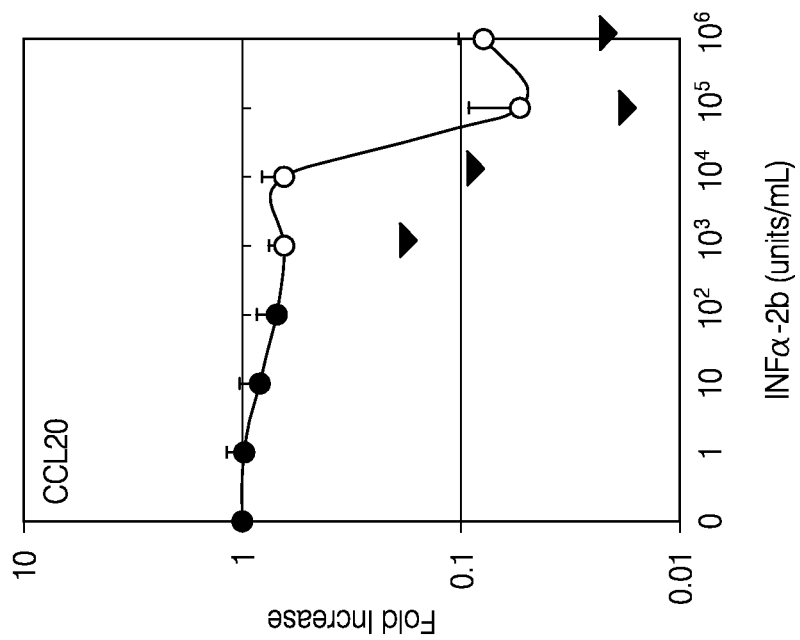
Figure 3B:
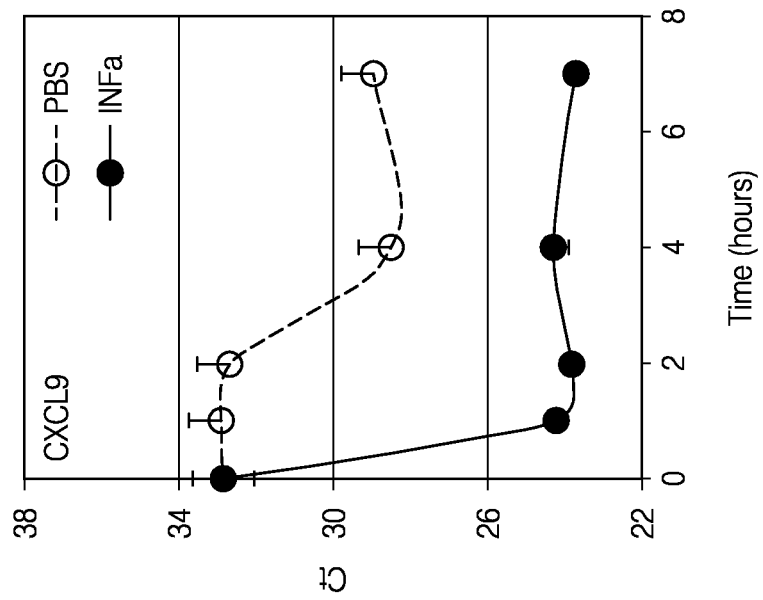
FIGS. 3A-3H. Ex vivo dose kinetic relationship between various mRNA expression and IFNα-2b stimulation. "○" represent PBS and "●" represent $10^5$ units/mL IFNα-2b. Each data point represents mean±s.d. (n=3).
Figure 3A:
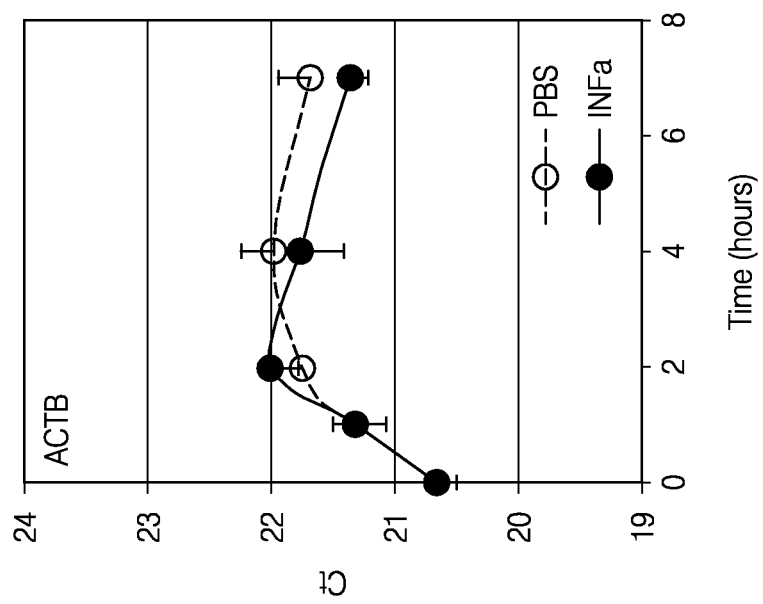
Figure 3D:
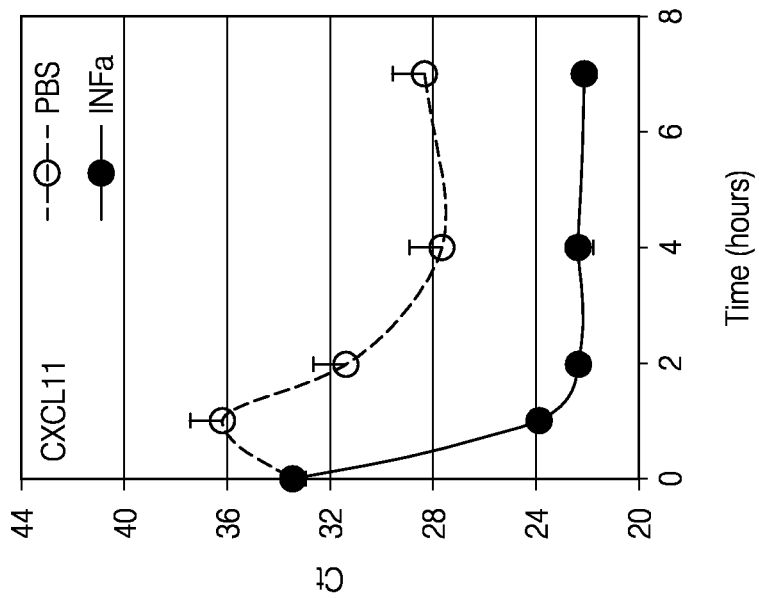
Figure 3C:
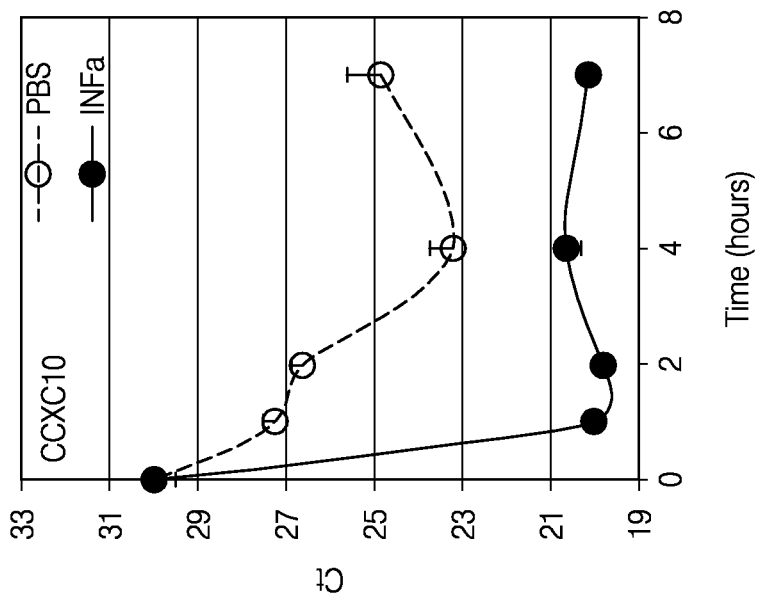
Figure 3F:
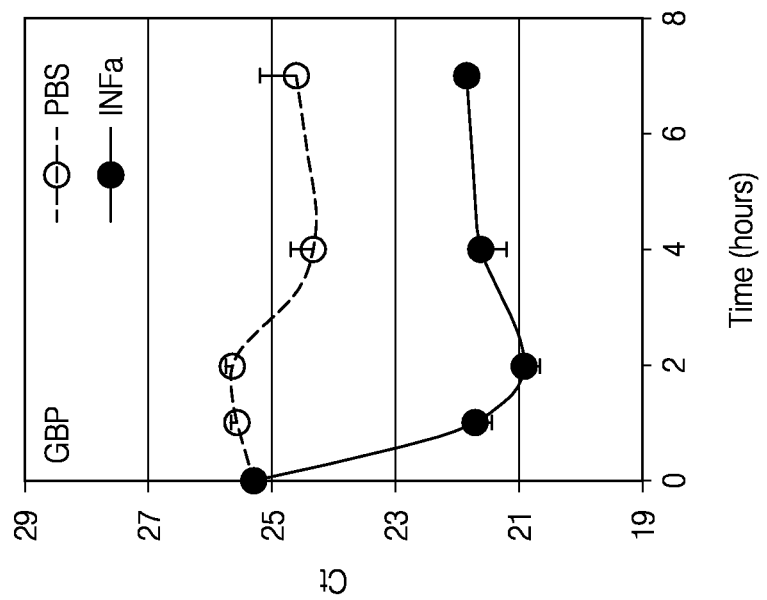
Figure 3E:
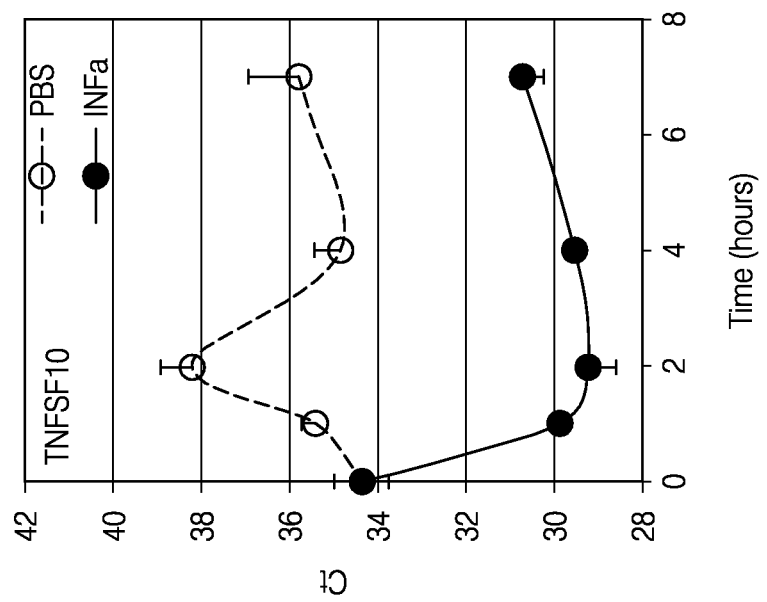
Figure 3H:
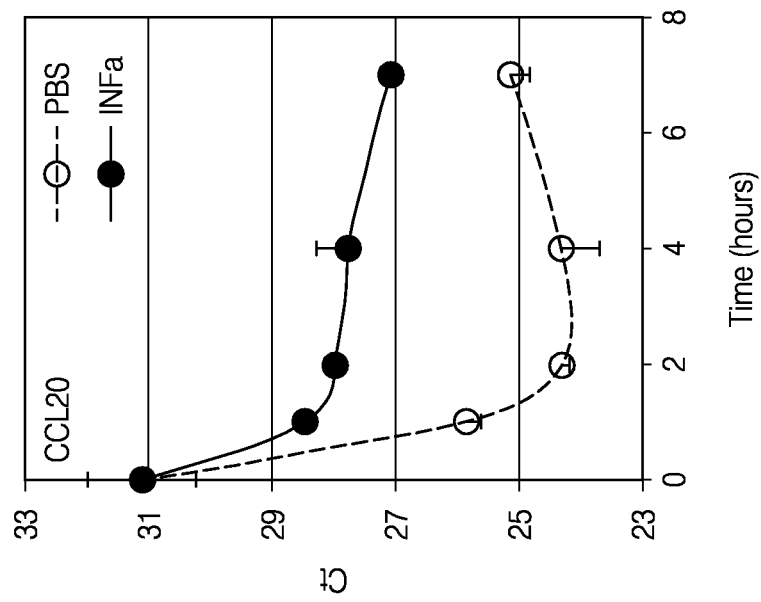
Figure 3G:
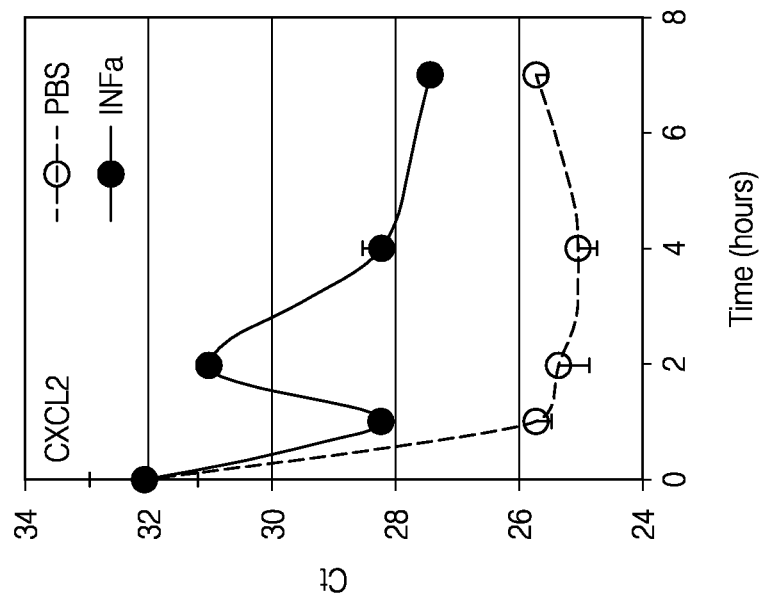
Figure 4D:
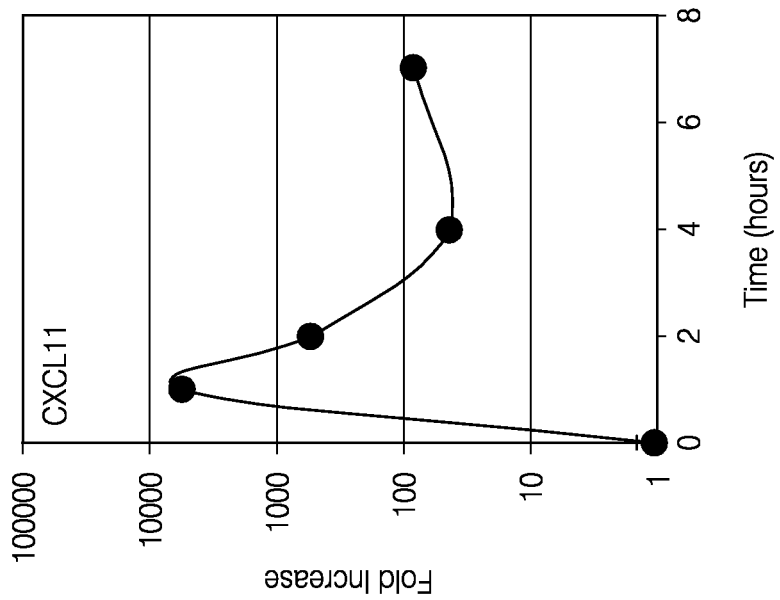
Figure 4C:
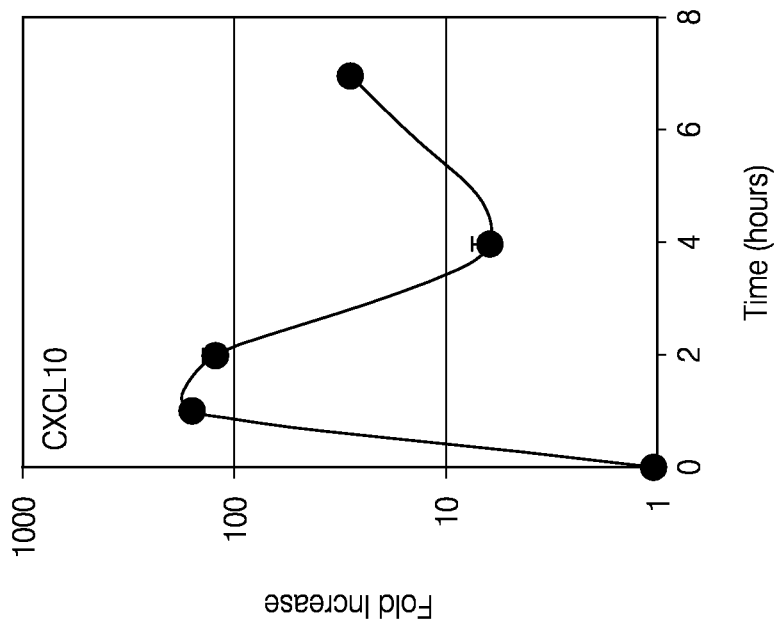
Figure 4F:
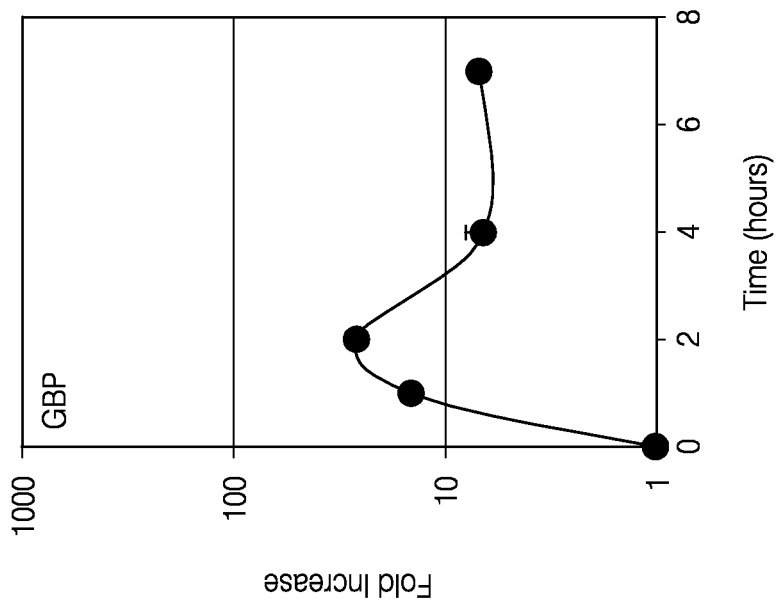
Figure 4E:
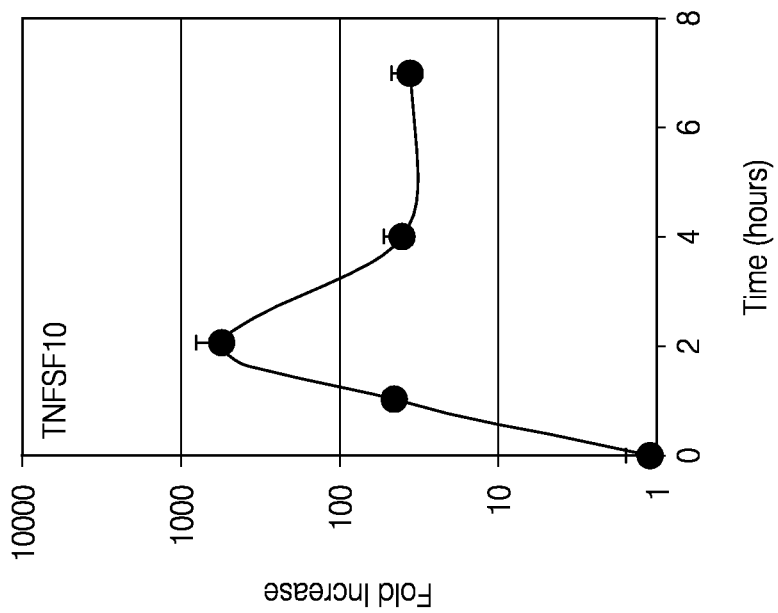
Figure 4H:
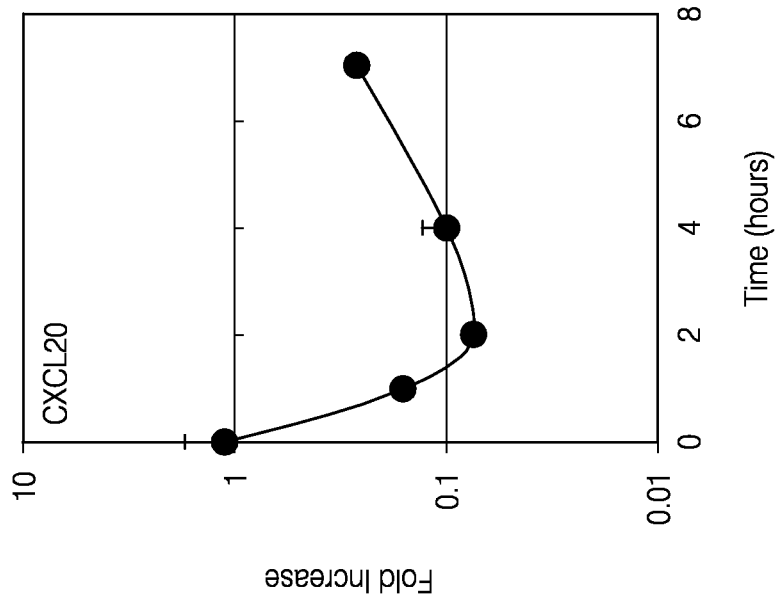
Figure 4G:
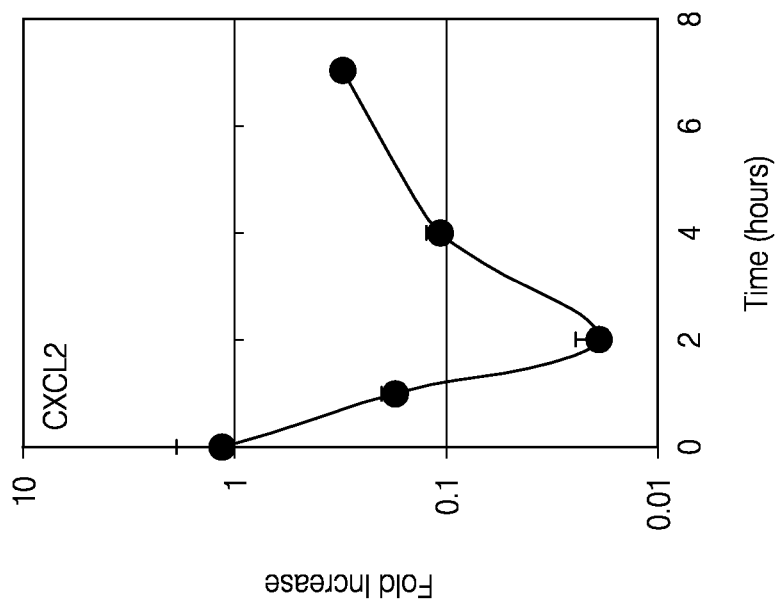

In several embodiments described herein, methods are provided for the ex vivo characterization of a host's responsiveness to administration of IFN. In several embodiments, the methods involve collection of peripheral whole blood from a potentially responsive individual and stimulation of the whole blood with IFN to screen for changes in expression of a panel of IFN-responsive markers. In several embodiments, detection of changes in the mRNA encoding one or more of the IFN-responsive markers is related to the individual's potential responsiveness to IFN administration. In other embodiments, methods are provided for the monitoring of the ongoing responsiveness of an individual to the administration of IFN. In some embodiments, peripheral whole blood is collected from an individual before and after administration of IFN, and evaluated for changes in expression of a panel of IFN-responsive markers. The changes in expression are then used to evaluate the individual's ongoing responsiveness to, and the efficacy of, IFN administration. In several embodiments, the methods described herein are used to predict the responsiveness to, or monitor the efficacy of, IFN administration in order to treat hepatitis infection or a related or unrelated malignancy. In some embodiments, the IFN administered to an individual is classified as a type I interferon, a type II interferon, or a type III interferon. In some embodiments, the interferon administered is chosen from the group consisting of IFN-alpha, IFN-beta, IFN-omega, IFN-gamma, combinations thereof, and subtypes thereof. In certain embodiments, the IFN administered is either IFN-alpha or IFN-gamma. In some such embodiments, the IFN-alpha is IFN-alpha-2b.

HBV is known to have infected approximately one-third of the world's population, more than 2 billion people. Of these infected individuals, over 350 million are chronic carriers of the virus. Acute hepatitis B can cause various symptoms, including liver inflammation, vomiting, jaundice, but rarely death. Chronic hepatitis B, however, may eventually lead to liver scarring (fibrosis and/or cirrhosis) and liver cancer, a cancer known to have poor responsiveness to chemotherapy regimes.

HBV can be classified into one of four major serotypes (adr, adw, ayr, ayw) based on the antigenic epitopes present on the viral proteins present on the exterior surface of the viral particle. Additionally, eight genotypes of HBV exist, according to overall nucleotide sequence variation of the HBV genome. Each genotype has a distinct geographical distribution and is often used for researching and cataloging the evolution and transmission of the virus. Clinically, however, variations between genotypes may greatly affect the severity of the infection, the overall response to treatment, recurrence of infection and risk of long term complications.

While acute hepatitis C infections are often asymptomatic, HCV has a high propensity to establish chronic infection and result in liver disease, which may include advanced scarring (cirrhosis). In some cases, those with cirrhosis will go on to develop liver failure or other complications of cirrhosis, including liver cancer. HCV has a rapid turnover rate within a host, and is also known to have error prone replication, which may play a role in allowing the virus to evade the host immune response for long periods of time.

Similarly to HBV, HCV exists in numerous different genotypes, with a total number ranging from six to eleven, depending on the classification methods used. Responsiveness of treatment varies across the genotypes, and can also affect the duration of treatment necessary to elicit a positive response against the infection.

IFN therapy, in various forms or combinations (including IFNα-2b), plays a critical role in the treatment of patients with hepatitis infections. It is often used in combination with various other therapeutic agents, but in patients who are unable to receive IFN, successful treatment is far more difficult. Further, chronic HCV infection is a major etiological component of hepatocellular carcinoma, a disease with an increasing prevalence worldwide. Studies have also shown that IFN treatment may reduce the occurrence of hepatocellular carcinoma, when used either alone or in conjunction with other agents.

IFN therapy is also used in other types of cancer, such as melanomas, hairy cell leukemia, and Kaposi's sarcoma, among others. In addition to the known immune-modulating and anti-viral functions, interferons are also considered anti-angiogenic, which may play a role in their anti-tumor activity. Mechanistically, IFNα-2b is thought to affect the JAK (Janus tyrosine kinase)/STAT (signal transducers and activators of transcription) signaling pathways. Specifically, down-regulation of STAT3 by IFNα-2b is associated with anti-tumor effects. However, numerous other molecules may be involved in the anti-viral and/or anti-tumor effects of IFN. For example, cytokines, interleukins and/or interleukin receptors, and a variety of signaling molecules may also play a role in the anti-viral and/or anti-tumor effects of IFN. Table 1 includes the primer sequences for a variety of molecules that, in certain embodiments, are involved in the anti-viral and/or anti-tumor effects of IFN.

Despite the beneficial therapeutic effects, side effects of IFN treatment may be severe. Symptoms can include decreased platelet count (which may lead to bleeding/bruising problems), depression, fatigue, increased risk of infection, post-administration flu-like symptoms (fever, chills, headache, muscle aches and pains, diarrhea), and possible tissue damage at sites of administration. Other documented side-effects include anorexia, congestion, increased heart rate, confusion, low white blood cell count, low red blood cell count, an increase in liver enzymes and/or triglycerides, skin rashes, mild hair loss, local and/or systemic swelling (edema), cough or difficulty breathing. Such side effects would be potentially harmful to a healthy individual, and could be devastating to an individual already suffering from an infection, a malignancy, or from side effects brought on by other therapeutic agents.

Thus, there exists a need for predicting if an individual will benefit from IFN therapy, as administration of IFN without positive effect would simply elicit unwanted and unnecessary side effects in patients non-responsive to IFN. Additionally, given the large number of people who have hepatitis or a form of cancer, a means to identify IFN responsive individuals would assist in providing tailored care to those who would benefit, and allowing non-responsive individuals to seek alternative therapeutic regimes that would be beneficial. Moreover, identification of markers that allow for categorization of responsive and non-responsive individuals would enable care-givers to monitor the efficacy of therapy in an on-going fashion, and may assist in the identification of individuals who develop a refractory response to IFN therapy.

Therefore, in several embodiments, methods are provided for the prediction of whether an individual may respond positively or negatively to the administration of IFN. In certain embodiments, the prediction is made in a clinical setting, while in other embodiments, the prediction is for research purposes.

In several embodiments, IFN stimulation of whole blood obtained from an individual (or IFN administration to the individual) alters the expression of one or more markers that are associated with one or more disease conditions. In certain embodiments, the expression of one or more of the markers is induced, while in other embodiments, the expression of one or more of the markers is down-regulated. In certain embodiments, the induction or down-regulation of the expression of one or more of the markers is statistically significant, as measured with standard statistical analyses with $p \leq 0.05$ representing a statistically significant change. In several embodiments, a significant increase in the expression of one or more IFN-responsive markers is an indication that an individual will be responsive to IFN administration. In several embodiments, a significant decrease in the expression of one or more IFN-responsive markers is an indication that an individual may fail to respond to IFN administration.

In some embodiments, the makers responsive to IFN, including IFNα-2b, administration include one or more of TNFSF (tumor necrosis factor super family) 1 (lymphotoxin α), TNFSF2, TNFSF5 (CD40), TNFRSF5 (CD40 receptor), TNFSF6 (Fas ligand), TNFSF8, TNFSF9, TNFSF10 (TRAIL—TNF-Related. Apoptosis-Inducing Ligand), TNFSF14, TNFSF15, CCL (Chemokine (C-C motif) ligand) 2, CCL3, CCL3, CCL8, CCL11, CCL20, CXCL (Chemokine (C-X-C motif) ligand) 1, CXCL2, CXCL3, CXCL5, CXCL9, CXCL10, CXCL 11, IL (interleukin) 1B, IL2, IL4, IL8, IL10, IL12A, IL17, IL23, FOXP3 (forkhead box P3), CD (Clusters of Differentiation) 25, CTLA4 (Cytotoxic T-Lymphocyte Antigen 4), Granzyme B, CD8A, CD16, CD32A, CD64, IgG Fc, ARG (arginase), MPO (myeloperoxidase), TLR (toll-like receptor) 2, TLR4, GM-CSF (granulocyte macrophage colony stimulating factor), IFNγ, TGF (transforming growth factor) β, CD4, STAT 1, STAT 3, STAT 4, VEGF (vascular endothelial growth factor), POMC (pro-opiomelanocortin), GBP (guanylate binding protein), XAF1 (X-linked inhibitor of apoptosis protein (XIAP)-associated factor 1), AIM2 (Absent in melanoma 2), SHP2, SOCS1 (suppressor of cytokine signaling-1), SLP76, G1P2 (ubiquitin-like modifier), BST2, IRF7 (interferon regulatory factor), and LCK.

In several embodiments the administration of IFN is for the treatment of viral infections. Certain embodiments are employed in the prediction of responsiveness to IFN administration in the treatment of hepatitis, including hepatitis B and C, among others. In several embodiments the administration of IFN is for the treatment of cancer. Certain embodiments are employed in the prediction of responsiveness to IFN administration in the treatment of cancers including, but not limited to hairy cell leukemia, chronic myelogenous leukemia, multiple myeloma, follicular myeloma, carcinoid tumors, and malignant melanoma. Certain other embodiments are employed in the prediction of responsiveness to IFN administration in the treatment of other types of cancers. In still other embodiments, IFN is administered for screening potentially efficacious drugs, rather than specifically treating an individual receiving the IFN or other potentially efficacious drug.

In several embodiments, blood is collected from mammals, preferably humans. In some embodiments, the blood collected is whole blood. Multiple experimental protocols directed to determining expression screening of markers responsive to a drug have been done in isolated leukocyte preparations. Such isolated populations are often preferred because the variety of lymphocytes in whole blood may preclude detection of induction of a specific mRNA in a small subset of lymphocytes. Moreover, with numerous complex biochemical interactions between the multiple types of lymphocytes, there is the possibility that use of a whole blood preparation inhibits or modifies the induction and measurement reactions. Furthermore, certain stimulatory agents (e.g., IFN) which are used in several embodiments, may interact with plasma proteins or plasma factors, and thereby exhibit decreased or reduced activity. However, when used as presented in several embodiments as described herein, whole blood unexpectedly produces reproducible, accurate, and physiologically relevant results that allow the characterization of the future or ongoing responsiveness of an individual to IFN. However, while preferred embodiments employ whole blood, in other embodiments, blood cells separated from plasma may also be used, as well as isolated leukocyte preparations.

In several preferred embodiments, the collected whole blood is heparinized upon collection. In several embodiments, the collected whole blood is stored at 4° C. until the stimulation protocol.

In several embodiments, the blood sample is combined with IFN and/or a control agent. In several embodiments, the control agent induces little or no response in the blood samples. In certain embodiments, the control agent is the same solvent used to carry the IFN. As discussed above, in some embodiments, various IFN are used, IFN-alpha, IFN-beta, IFN-omega, IFN-gamma, combinations thereof, and subtypes thereof. In certain embodiments, the control agent is phosphate-buffered saline (PBS). In other embodiments, other inert control agents may be used such as control IgG (serving as a control for those stimulating agents that are antibodies) or DMSO. In several embodiments, on the same day of blood draw, a small volume of whole blood is combined with IFN (or control agent) and incubated at 37° C. for a period of time. In some embodiments, the incubation period is about 4 hours. In some embodiments, incubation is for greater than 4 hours, while in other embodiments, incubation is for less than 4 hours. After incubation, all blood samples are stored frozen at −80° C. until analysis.

In several embodiments, a small volume of the previously stimulated blood from each sample is processed to allow determination of the levels of mRNA encoding one or more IFN markers in the blood. In some embodiments, the levels of mRNA encoding one or more IFNα responsive markers will change significantly in response to the IFN incubation. To determine these mRNA levels, the erythrocytes and blood components other than leukocytes are removed from the whole blood sample. In preferred embodiments, the leukocytes are isolated using a device for isolating and amplifying mRNA. Embodiments of this device are described in more detail in U.S. patent application Ser. Nos. 10/796,298, 11/525,515, 11/376,018, 11/803,593, 11/803,594, and 11/803,663, each of which is incorporated in its entirety by reference herein.

In brief, certain embodiments of the device comprise a multi-well plate that contains a plurality of sample-delivery wells, a leukocyte-capturing filter underneath the wells, and an mRNA capture zone underneath the filter which contains immobilized oligo(dT). In certain embodiments, the device also contains a vacuum box adapted to receive the filter plate to create a seal between the plate and the box, such that when vacuum pressure is applied, the blood is drawn from the sample-delivery wells across the leukocyte-capturing filter, thereby capturing the leukocytes and allowing non-leukocyte blood components to be removed by washing the filters. In other embodiments, other means of drawing the blood samples through out of the sample wells and through the across the leukocyte-capturing filter, such as centrifugation or positive pressure, are used. In preferred embodiments of the device, leukocytes are captured on a plurality of filter membranes that are layered together. In several embodiments, the captured leukocytes are then lysed with a lysis buffer, thereby releasing mRNA from the captured leukocytes. The mRNA is then hybridized to the oligo(dT)-immobilized in the mRNA capture zone. Further detail regarding the composition of lysis buffers that may be used in several embodiments can be found in U.S. patent application Ser. No. 11/376,018, filed Mar. 15, 2006, which is currently pending and which is incorporated in its entirety by reference herein. In several embodiments, cDNA is synthesized from oligo(dT)-immobilized mRNA. In preferred embodiments, the cDNA is then amplified using real time PCR with primers specifically designed for amplification of infection-associated markers. Primers that are used in such embodiments are shown in Table 1. Further details about the PCR reactions used in some embodiments are also found in U.S. patent application Ser. No. 11/376,018.

TABLE 1

Primer Sequences for RT-PCR Amplification

| Target | Seq Id. No. | FWD Sequence (5'-3') | Seq Id. No. | REV Sequence (3'-5') |
|---|---|---|---|---|
| B-Actin | 1 | CCTGGCACCCAGCACAAT | 2 | GCCGATCCACACGGAGTACT |
| B-2 microglobulin (B2M) | 3 | TGACTTTGTCACAGCCCAAGATA | 4 | AATGCGGCATCTTCAAACCT |
| GAPDH | 5 | AAGGACTCAT GACCACAGTC CAT | 6 | CCATCACGCCACAGTTTCC |
| TNFSF1 | 7 | CAGCTATCCACCCACACAGATG | 8 | CGAAGGCTCCAAAGAAGACAGT |
| TNFSF2 | 9 | CGAAGGCTCCAAAGAAGACAGT | 10 | CAGGGCAATGATCCCAAAGT |
| TNFSF5 | 11 | CCACAGTTCCGCCAAACCT | 12 | CACCTGGTTGCAATTCAAATACTC |
| TNFRSF5 | 13 | GGCCAAGAAGCCAACCAATA | 14 | GAAGATCGTCGGGAAAATTGAT |
| TNFSF6 | 15 | TGGCAGCATCTTCACTTCTAAATG | 16 | GAAATGAGTCCCCAAAACATCTCT |
| TNFSF8 | 17 | ACCACCATATCAGTCAATGTGGAT | 18 | GAAGATGGACAACACATTCTCAAGA |
| TNFSF9 | 19 | AGCTACAAAGAGGACACGAAGGA | 20 | CGCAGCTCTAGTTGAAAGAAGACA |
| TNFSF10 | 21 | GGGAATATTTGAGCTTAAGGAAAATG | 22 | AAAAGGCCCCGAAAAAACTG |
| TNFSF14 | 23 | CGTCCGTGTGCTGGATGA | 24 | CATGAAAGCCCCGAAGTAAGAC |
| TNFSF15 | 25 | TGCGAAGTAGGTAGCAACTGGTT | 26 | CCATTAGCTTGTCCCCTTCTTG |
| CCL2 | 27 | CCATTGTGGCCAAGGAGATC | 28 | TGTCCAGGTGGTCCATGGA |
| CCL3 | 29 | CACAGAATTTCATAGCTGACTACTTTGA | 30 | TCGCTTGGTTAGGAAGATGACA |
| CCL4 | 31 | GGTATTCCAAACCAAAAGAAGCA | 32 | GTTCAGTTCCAGGTCATACACGTACT |
| CCL8 | 33 | AGAGCTACACAAGAATCACCAACATC | 34 | AGACCTCCTTGCCCCGTTT |
| CCL11 | 35 | CCCAGAAAGCTGTGATCTTCAA | 36 | TCCTGCACCCACTTCTTCTTG |
| CCL20 | 37 | GATACACAGACCGTATTCTTCATCCTAA | 38 | TGAAAGATGATAGCATTGATGTCACA |
| CXCL1 | 39 | CCACTGCGCCCAAACC | 40 | GCAGGATTGAGGCAAGCTTT |
| CXCL2 | 41 | CCCCTGGCCACTGAACTG | 42 | TGGATGTTCTTGAGGTGAATTCC |
| CXCL3 | 43 | GGAATTCACCTCAAGAACATCCA | 44 | GTGGCTATGACTTCGGTTTGG |
| CXCL5 | 45 | AGAGCTGCGTTGCGTTTGT | 46 | TGGCGAACACTTGCAGATTACT |
| CXCL9 | 47 | CCACCTACAATCCTTGAAAGACCTT | 48 | CAGTGTAGCAATGATTTCAATTTTCTC |
| CXCL10 | 49 | TCCACGTGTTGAGATCATTGC | 50 | TCTTGATGGCCTTCGATTCTG |
| CXCL11 | 51 | AGGACGCTGTCTTTGCATAGG | 52 | GCATCGTTGTCCTTTATTTTCTTTC |
| IL1B | 53 | GAAGATGGAAAAGCGATTTGTCTT | 54 | GGGCATGTTTTCTGCTTGAGA |
| IL2 | 55 | GAACTAAAGGGATCTGAAACAACATTC | 56 | TGTTGAGATGATGCTTTGACAAAA |
| IL4 | 57 | CACAGGCACAAGCAGCTGAT | 58 | CCTTCACAGGACAGGAATTCAAG |
| IL8 | 59 | TGCTAAAGAACTTAGATGTCAGTGCAT | 60 | TGGTCCACTCTCAATCACTCTCA |
| IL10 | 61 | GCCATGAGTGAGTTTGACATCTTC | 62 | GATTTTGGAGACCTCTAATTTATGTCCTA |
| IL12A | 63 | GCAGGCCCTGAATTTCAACA | 64 | GAAGTATGCAGAGCTTGATTTTAGTTTTA |
| IL17 | 65 | CATGAACTCTGTCCCCATCCA | 66 | TCCAGCCGGAAGGAGTTG |
| IL23 | 67 | CAGCAACCCTGAGTCCCTAAAG | 68 | TTGCTGGGCCATGGAGAT |
| FOXP3 | 69 | CACCTACGCCACGCTCATC | 70 | AAGGCAAACATGCGTGTGAA |
| CD25 | 71 | CAGAAGTCATGAAGCCCAAGTG | 72 | GGCAAGCACAACGGATGTCT |

TABLE 1-continued

Primer Sequences for RT-PCR Amplification

| Target | Seq Id. No. | FWD Sequence (5'-3') | Seq Id. No. | REV Sequence (3'-5') |
|---|---|---|---|---|
| CTLA4 | 73 | CATGCCTCCTCTTCTTCCTTGA | 74 | GGAGGGTGCCACCATGACTA |
| Granzyme B | 75 | GCGGTGGCTTCCTGATACAA | 76 | CCAAGGTGACATTTATGGAGCTT |
| CD8A | 77 | CCGAGAGAACGAGGGCTACTATT | 78 | GCACGAAGTGGCTGAAGTACAT |
| CD16 | 79 | GTTTGGCAGTGTCAACCATCTC | 80 | AAAAGGAGTACCATCACCAAGCA |
| CD32A | 81 | GCTGACGGCGGCTACATG | 82 | GAGGAAGAGTCAGGTAGATGTTTTTATCA |
| CD64 | 83 | CTGGCAGTGGGAATAATGTTTTT | 84 | CACTTTTTCTTTCTTTTCAGTTCTTTGCG |
| IgG Fc | 85 | CAGCCGGAGAACAACTACAAGAC | 86 | GCTGCCACCTGCTCTTGTC |
| ARG | 87 | AGACACCAGAAGAAGTAACTCGAACA | 88 | TCCCGAGCAAGTCCGAAAC |
| MPO | 89 | ACTGCCTGGGTTCCAATCC | 90 | TGTTTAAGGAGGGTAATTTGCTCAA |
| TLR2 | 91 | GAAGAGTGAGTGGTGCAAGTATGAA | 92 | ATGGCAGCATCATTGTTCTCATC |
| TLR4 | 93 | GATTGCTCAGACCTGGCAGTT | 94 | TGTCCTCCCACTCCAGGTAAGT |
| GM-CSF | 95 | GGCCCCTTGACCATGATG | 96 | TCTGGGTTGCACAGGAAGTTT |
| IFNγ | 97 | GGAGACCATCAAGGAAGACATGA | 98 | GCTTTGCGTTGGACATTCAA |
| TGFβ | 99 | CTGCTGAGGCTCAAGTTAAAAGTG | 100 | TGAGGTATCGCCAGGAATTG T |
| CD4 | 101 | AAATGCCACACGGCTCTCA | 102 | GGGTGCTGTGCTTCTGTGAAC |
| STAT 1 | 103 | GTGGAAAGACAGCCCTGCAT | 104 | ACTGGACCCCTGTCTTCAAGAC |
| STAT 3 | 105 | GCCAGAGAGCCAGGAGCAT | 106 | GGTGTCACACAGATAAACTTGGTCTT |
| STAT 4 | 107 | CATTTGGTACAACGTGTCAACCA | 108 | TGTGGCAGGTGGAGGATTATTA |
| VEGF | 109 | CGCAGCTACTGCCATCCAAT | 110 | TGGCTTGAAGATGTACTCGATCTC |
| POMC | 111 | ACGAGGGCCCCTACAGGAT | 112 | TGATGATGGCGTTTTTGAACA |
| GBP | 113 | AGAAGTGAAGGCGGGAATTTATT | 114 | ATCCCCTTCCTCGGTTCCT |
| XAF1 | 115 | CCTAGAGGAGATAAAGCAGCCTATGA | 116 | AAGCTAACCACCGGCATTTCT |
| AIM2 | 117 | GGTGAAACCCCGAAGATCAA | 118 | CTGGACTACAAACAAACCATTCACA |
| SHP2 | 119 | TCCAGATGGTGCGGTCTCA | 120 | CCTGCGCTGTAGTGTTTCAATATAA |
| SOCS1 | 121 | GGAACTGCTTTTTCGCCCTTAGC | 122 | CTGAAAGTGCACGCGGATGCT |
| SLP76 | 123 | CCGTTATCAGAAGGAAAGTCAAGTT | 124 | ATATCTGACACAGACAGAAAGTCCTCTT |
| G1P2 | 125 | CAAATGCGACGAACCTCTGA | 126 | CCGCTCACTTGCTGCTTCA |
| BST2 | 127 | GAGATCACTACATTAAACCATAAGCTTCAG | 128 | TCTCACGCTTAAGACCTGGTTTT |
| IRF7 | 129 | TCCCCACGCTATACCATCTACCT | 130 | ACAGCCAGGGTTCCAGCTT |
| LCK | 131 | TTAAGTGGACAGCGCCAGAA | 132 | CCCAAAAGACCACACATCTGACT |

After the completion of PCR reaction, the mRNA (as represented by the amount of PCR-amplified cDNA detected) for one or more IFN markers is quantified. In certain embodiments, quantification is calculated by comparing the amount of mRNA encoding one or more IFN markers to a reference value. In several embodiments, the reference value is a non-stimulated sample (e.g., a solvent control-exposed blood sample). In other embodiments, the reference value is expression level of a gene that is not induced by the stimulating agent, e.g., a house-keeping gene. In certain such embodiments, beta-actin is used as the reference value. Numerous other house-keeping genes that are well known in the art may also be used as a reference value. In other embodiments, a house keeping gene is used as a correction factor, such that the ultimate comparison is the induced expression level of one or more IFN markers as compared to the same marker from a non-induced (control) sample. In still other embodiments, the reference value is zero, such that the quantification of one or more IFN markers is represented by an absolute number. In several embodiments a ratio comparing the expression of one or more IFN-responsive markers to a solvent control is made. In still other embodiments, no normalization is made. In some embodiments, a first sample from a subject is exposed to interferon in a solvent and a second sample is exposed to the solvent without the interferon. The effect of the interferon is then quantified by calculating the change in expression of one or more interferon-responsive markers by measuring the amount of mRNA encoding those markers in both the first and second samples from the subject. That quantified effect, in several embodiments, is then compared to the normal effect that interferon exposure has on expression of one or more interferon-responsive markers. The normal effect is calculated as the change in expression between two samples (interferon and solvent control) taken from a panel of control individuals (e.g., an average change in expression in one or more markers measured from a plurality of individuals). Finally, the potential responsiveness of the subject is characterized by identifying significant differences between the quantified expression changes the subject's sample and the average change in expression of the interferon-responsive markers in from the panel of control individuals. Potential responsiveness to interferon is identified by changes in expression in the subject that are substantially greater than changes from the panel of control individuals. Potential non-responsiveness is identified by changes in expression in the subject that is substantially less than the changes from the panel of control individuals.

In several embodiments, the methods described herein are used to monitor an individual's responsiveness to ongoing IFN administration. In some such embodiments, a first blood sample is obtained from the individual. In some embodiments, the first blood sample is obtained prior to the administration of any IFN to the individual. In other embodiments, the individual has received IFN in the past, and will again in the future. In some embodiments, the first blood sample is obtained at a time between two administrations of IFNα-2b, preferably just prior to an administration. A second blood sample is obtained from the individual at a time after the administration of IFN. In certain embodiments, this time is several hours, though in other embodiments, the time is several weeks, and in some embodiments up to several months. In other embodiments, additional samples are taken serially over the course of several months. The blood samples obtained from the individual are then frozen until expression analysis, which is performed as described above. Evaluation of expression levels of IFN responsive markers can thus be used to monitor the progress (i.e., efficacy) of IFN administration. In some embodiments, a significant difference in expression of one or more IFN responsive markers between the post-IFN administration blood sample and the pre-IFN administration blood sample indicates that therapy is effective. In other embodiments, a lack of any significant difference in expression of one or more IFN responsive markers between the post-IFN and pre-IFN administration blood samples indicates that therapy is not effective. In still other embodiments, this protocol is adapted to monitor the efficacy of other putative therapeutic agents.

EXAMPLES

Specific embodiments will be described with reference to the following examples which should be regarded in an illustrative rather than a restrictive sense.

Example 1

Ex Vivo Screening of Markers Responsive to IFNα-2b

Blood was drawn into a heparin tube from a single healthy donor and was stored at 4° C. until use. On the same day as the blood draw, IFNα-2b (stock concentration of $5 \times 10^6$ units/mL) was diluted 1:10 with PBS, and 1.2 µL of the diluted IFNα-2b was dispensed into 3 wells and PBS were dispensed into another 3 wells of a single 8-well tube strip. Sixty (60) µL each of stored whole blood sample was then added into all 6 wells (triplicate for both IFNα-2b and PBS), and incubated at 37° C. for 4 hours. After incubation, all blood samples were stored frozen at −80° C. Various mRNA were quantified by using SYBR green real time PCR as described previously (Mitsuhashi M et al. Clin. Chem. 52:634-642, 2006).

Briefly, 96-well filterplates were assembled with leukocyte reduction membranes (Leukosorb; Pall) and placed over oligo(dT)-immobilized collection plates. 150 µL of 5 mmol/L Tris (pH 7.4) was applied to wet the filter membranes. After centrifugation at 120 g for 1 min at 4° C. to remove the Tris solution from the membranes, 50 µL of the stimulated whole blood samples was applied to each well and immediately centrifuged at 120 g for 2 min at 4° C. The wells were then washed once with 300 µL of phosphate-buffered saline. After centrifugation at 2000 g for 5 min at 4° C. to remove the saline solution, 60 µl of stock lysis buffer [5 g/L N-lauroylsarcosine, 4× standard saline citrate, 10 mmol/L Tris-HCl (pH 7.4), 1 mmol/L EDTA, 1 mL/L IGEPAL CA-630 (substitute of NP-40), 1.79 mol/L guanidine thiocyanate (all from Sigma)], supplemented with 10 mL/L 2-mercaptoethanol (Bio-Rad), 0.5 g/L proteinase K (Pierce), 0.1 g/L salmon sperm DNA (5 Prime Eppendorf/Brinkman), 0.1 g/L *Escherichia coli* tRNA (Sigma), 5 nmol/L each of the specific reverse primers, and $10^{10}$ molecules/L of synthetic RNA34 (as external control), was added to each well of the filterplates. The plates were then incubated at 37° C. for 10 min, placed over oligo(dT)-immobilized collection microplates (GenePlate; RNAture), and centrifuged at 2000 g for 5 min at 4° C. After overnight storage at 4° C., the microplates were washed 3 times with 100 µL of plain lysis buffer and then 3 times with 150 µL of wash buffer [0.5 mol/L NaCl, 10 mmol/L Tris (pH 7.4) 1 mmol/L EDTA] at 4° C.

cDNA was synthesized directly in each well by addition of 30 µL of buffer containing 1× reverse transcription buffer [50 mM KCl, 10 mM Tris-HCl (pH 8.3), 5.5 mM $MgCl_2$, 1 nL/µL Tween 20], 1.25 mM each deoxynucleoside triphosphate, 4 units of rRNasin, and 80 U of MMLV reverse transcriptase (Promega; without primers) and incubation at 37° C. for 2 h. From each 30-µL reaction, 4 µL of cDNA was transferred directly to 384-well PCR plates, and 5 µL of TaqMan universal master mixture (Applied Biosystems) and 1 µL of 5 µM each of the forward and reverse primers for IFN-induced markers or beta-actin (see Table 1) were added. PCR was carried out in a PRISM 7900HT (Applied Biosystems), with 1 cycle of 95° C. for 10 min followed by 45 cycles of 95° C. for 30 s, 55° C. for 30 s, and 60° C. for 1 min. Each gene was amplified in separate wells. The cycle threshold (Ct), i.e., the cycle at which certain amounts of PCR products (based on fluorescence) were generated, was determined with analytical software (SDS; Applied Biosystems). The ΔCt were determined by subtracting each Ct of IFNα-2b treated sample from each Ct of PBS-treated control sample, and the fold increase was calculated by 2^−ΔCt.

As shown in FIG. 1, the three housekeeping gene (ACTB, B2M, and GAPDH) samples stimulated with IFNα-2b were all within 0.5-2 fold change from their respective control samples, indicating no significant changes in expression in response to IFNα-2b stimulation. In contrast, significant increases in expression were detected in TNFSF1, TNFRSF5, TNFSF6, CCL8, CXCL9, CXCL10, CXCL11, IFNγ, STAT1, GBP (common for both 1 and 2), XAF1, SOCS1, G1P2, BST2, and IRF7. Significant decreases in expression were calculated for TNFSF5, TNFSF8, TNFSF14, TNFSF15, CCL3, CCL20, CXCL1, CXCL2, CXCL3, CXCL5, IL1B, IL8, IL10, IL23, TLR2, VEGF, and LCK. Though TNFSF10, granzyme B, CD64, and MPO all displayed trends toward significantly increased expression, the calculated increase was not statistically significant. These results indicate that a large number of cytokines, immune response elements, signaling factors, and other categories of markers are significantly responsive to IFNα-2b stimulation.

Example 2

Dose Response to Ex Vivo Stimulation with IFNα-2b

Based on the results of Example 1, selected markers that were responsive to IFNα-2b were evaluated with respect to the change in expression as related to the dose of IFNα-2b used to stimulate the whole blood sample.

Whole blood collected as described above was stimulated with various doses of IFNα-2b ranging from 0 to $10^6$ units/mL for 4 hours, then stored frozen at −80° C. until analysis. Analysis was performed as described above, the results of which are shown in FIG. 2.

As shown in FIG. 2, IFNα-2b stimulation induced a dose dependent increase in CXCL9, CXCL10, CXCL11, GBP1/2, and TNFSF10. Similarly, a dose dependent decrease in expression was detected for CXCL2 and CCL20. The effects of IFNα-2b stimulation appeared to plateau at approximately $10^5$-$10^6$ units/mL of IFNα-2b. Additionally, it appears that IFNγ gene expression may respond to IFNα-2b in a narrow concentration range at or around $10^5$ units/mL of IFNα-2b. These experiments suggest that $10^5$ units/mL of IFNα-2 may be an optimal concentration for eliciting gene expression changes in responsive markers. The eight markers used in Example 2 were also used in Example 3.

Example 3

Kinetic Response to Ex Vivo Stimulation with IFNα-2b

Based on the results of Example 2, eight markers that were responsive to IFNα-2b at a dose of $10^5$ units/mL of IFNα-2 were evaluated with respect to the kinetics expression changes after stimulation of the whole blood sample.

Whole blood collected as described above was stimulated with $10^5$ units/mL of IFNα-2 (or with PBS alone) for times ranging from 0 to 7 hours, then stored frozen at −80° C. until analysis. mRNA expression analysis was performed as described above, the results of which are shown in FIGS. 3 (Ct) and 4 (fold change).

As shown in FIG. 3, Ct values of beta-actin (ACTB) were unchanged between PBS (○) and IFNα-2b (●) over the 7 hour incubation. However, $10^5$ units/mL IFNα-2b induced significant induction in the expression of CXCL9, CXCL10, CXCL11, TNFSF10, GBP mRNAs, as depicted by the Ct of IFNα-2b-treated samples being lower than that of PBS controls. In contrast, IFNα-2b significantly decreased the levels of CXCL2 and CCL20 mRNA. Significant changes were seen as early as 1 hour incubation. Changes in expression (both increase and decrease) of these mRNAs occurred rapidly after the initial stimulation. Expression changes appeared to peak around 1-2 hours, and reach a steady state of expression after about 4 hours. Based on these data, 4 hours was chosen as the incubation time for further analysis.

Example 4

Ex Vivo IFNα-2b Stimulation

Figure 5:
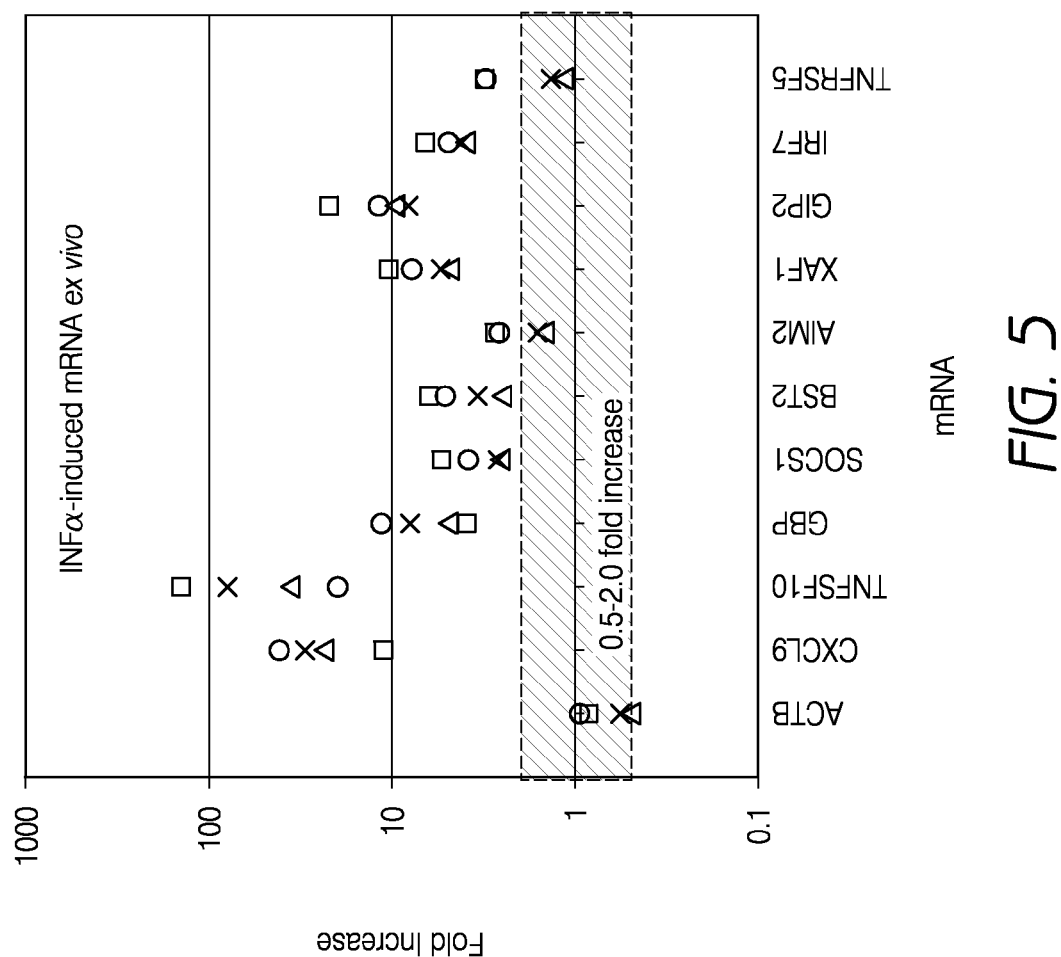
FIG. 5. Ex vivo mRNA expression after IFNα-2b stimulation. Each data point (○: Pt. #1, Δ: Pt. #2, x: Pt. #3, □: Pt. #4) represents mean values FIG. 6. Relationship between mRNA expression and in vivo IFNα-2b stimulation. Each data point (○: Pt. #1, Δ: Pt. #2) represents mean values (n=9). Significant increases are denoted by a "*" and significant decreases by a "▼". Blanket: fold increase between 0.5 and 2.

Whole blood was collected from four adult donors as described above. Blood samples were stimulated with $10^5$ units/mL of IFNα-2 for 4 hours at 37° C., then stored frozen at −80° C. until analysis. mRNA expression analysis was performed as described above, the results of which are shown in FIG. 5.

Expression of the housekeeping gene beta actin was not significantly changed by stimulation with IFNα-2. In contrast, nearly all of the mRNAs measured in each of the four individuals were significantly induced by stimulation with IFNα-2. This suggests that all four individuals are potentially responsive to IFNα-2 therapy. Even with increases detected in most mRNAs analyzed, there was substantial individual to individual variation. This may indicate that even with IFNα-2-responsive populations, there is variation in the degree of responsiveness. For example, Patient #4 (□) appears to have a more robust increase in mRNA levels for many of the mRNAs evaluated, suggesting that this individual may be more highly responsive to IFNα-2.

Example 5

In Vivo Response to IFNα-2b Administration

Figure 6:
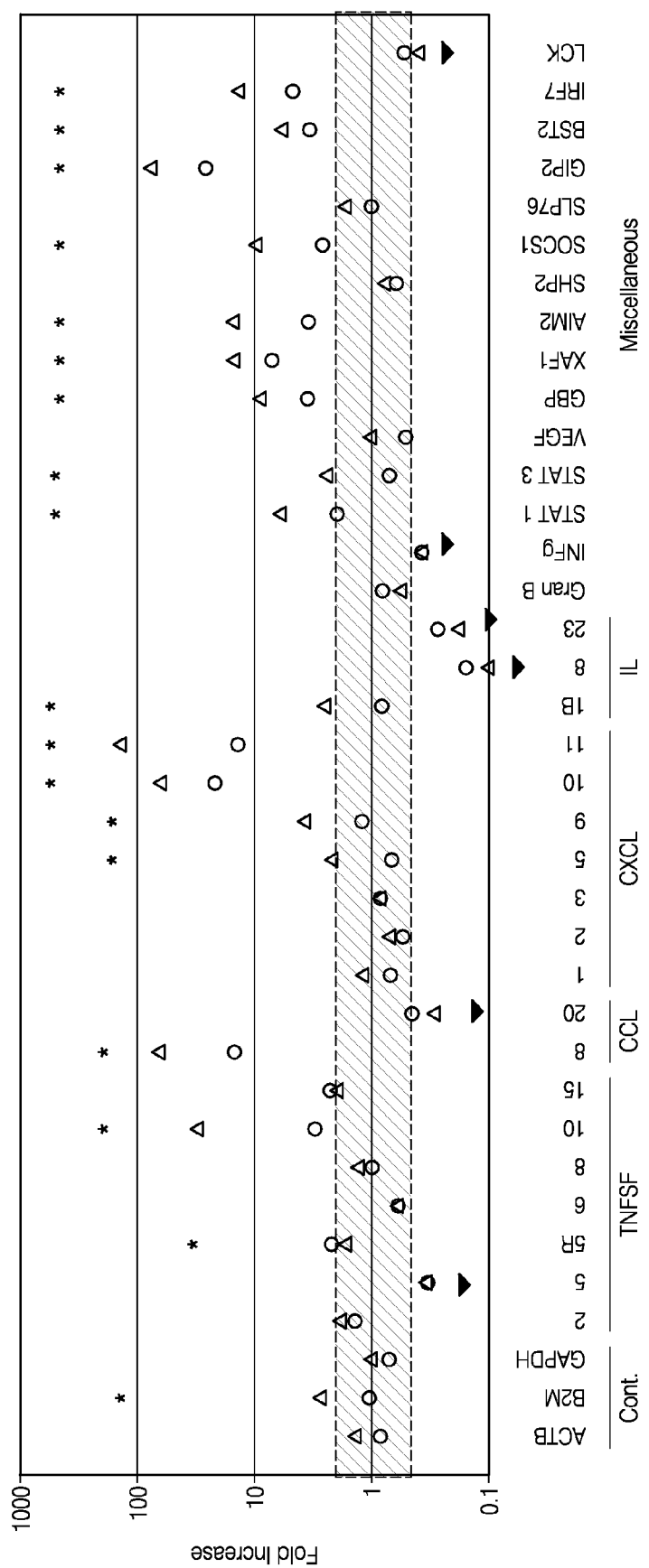

Whole blood was obtained from two patients receiving ongoing IFNα-2b therapy. Two samples were obtained from each patient, a first sample prior to administration of IFNα-2b, and a second sample 24 hours after IFNα-2b administration. RNA was isolated by the PAXgene method according to the manufacturer's protocol. Results are shown in FIG. 6 and Table 2. For these patient samples, no normalization was made when calculating the fold change in expression, as the expression levels of one housekeeping gene, B-2 microglobulin, was greater than 2 fold between the pre-IFNα-2b and post-IFNα-2b samples.

As shown in FIG. 6, TNFRSF5, CCL8, CXCL10, CXCL11, STAT1, GBP, XAF1, AIM2, SOCS1, G1P2, BST2, and IRF7 were induced significantly by the administration of IFNα-2b in both Patient #1 and Patient #2. In contrast, expression of TNFSF5, IL8, IL23, and LCK mRNAs were decreased significantly in both cases after administration of IFNα-2b. For several markers, Patient #2 showed a greater change in expression after IFNα-2b administration as compared to Patient #1. Table 2 shows the various mRNA species influenced by IFNα-2b administration in vivo and the influence of IFNα-2b stimulation ex vivo. The results of ex vivo studies were well correlated to those of in vivo studies. As shown in Table I, CCL8, CXCL9, CXCL10, CXCL11, GBP, XAF1, SOCS1, G1P2, BST2, and IRF7 are reliable markers of IFNα-2b-mediated increase, and TNFSF5, IL8, and IL23 were reliable markers of IFNα-2b-mediated decrease. The remaining markers that did not show a clear correlation based on these experiments are undergoing further study to determine if optimization of the current experimental protocol or an alternative protocol is necessary to establish a correlation.

However, based on the correlations established through Examples 1-3, certain embodiments of the ex vivo stimulation and analysis presented herein provide a diagnostic test for the prediction of responders/non-responders for INFα-2b therapy. Likewise, the certain embodiments of the in vivo analysis presented herein provide a diagnostic test for the monitoring of INFα-2b therapy.

Example 6

Use of Other Interferons

The experiments described in Examples 1-4 are repeating using INFγ and other interferons in place of INFα-2b. Similar results are observed.

Example 7

Characterizing Host Responsiveness to Interferon by Ex Vivo Induction of Interferon-Responsive mRNAs Interferons (IFN) can be effective clinically for patients with infectious diseases (hepatitis B and C), autoimmune disorders (multiple sclerosis) and malignant neoplasms (leukemia, lymphoma, melanoma). However, there remains a need for assessing the likelihood that a given individual will respond to IFN administration and to assess pharmacodynamics of response. In the present example, triplicate aliquots of 0.06 ml each of heparinized whole blood were stimulated with IFNs (IFNα2b, IFN β-1a, IFN γ) or solvent control for only 2 hours, then various IFN-responsive mRNAs were quantified by a high throughput assay. Significant induction was identified for CCL chemokine-8, CXCL chemokine-9, 10, 11, tumor necrosis factor superfamily (TNFSF)-10, guanylate binding protein 1 (GBP1), XIAP associated factor 1 (XAF1), suppressor of cytokine signaling 1 (SOCS1), ISG15 ubiquitin-like modifier (ISG15, G1P2), bone marrow stromal cell antigen 2 (BST2), and interferon regulatory factor 7 (IRF7), whereas the levels of TNFSF5, interleukin (IL)-8, and IL23 were decreased. The increase or decrease of these mRNAs happened rapidly, and reached a plateau after 2-4 hours. The reaction was dose dependent from $10^4$-$10^5$ units/ml of IFNα2b. To confirm the ex vivo results, blood was drawn into PAXgene tubes before and after IFNα2b under an IRB-approved protocol. Total RNA was extracted from nucleated cells and used to measure mRNAs using the same method as the ex vivo assay. As a result, the increase and decrease of above mentioned mRNAs were confirmed in this in vivo assay. Within 4 hours after IFN administration, more than 32 folds induction of TNFSF10, SOCS1, CXCL10, CXCL11, G1P2, and GBP1 mRNA were identified. Moreover, the levels of these mRNA markers changed during clinical course, suggesting that the assay can be used to monitor host responsiveness to IFN and/or other therapies and immunomodulators. The throughput seamless process of the assay allows manipulation of many samples simultaneously, and small variation among triplicate samples provides sensitivity to detect 50% change with statistical significance for each mRNA.

Methods
Ex Vivo

Figure 7A:
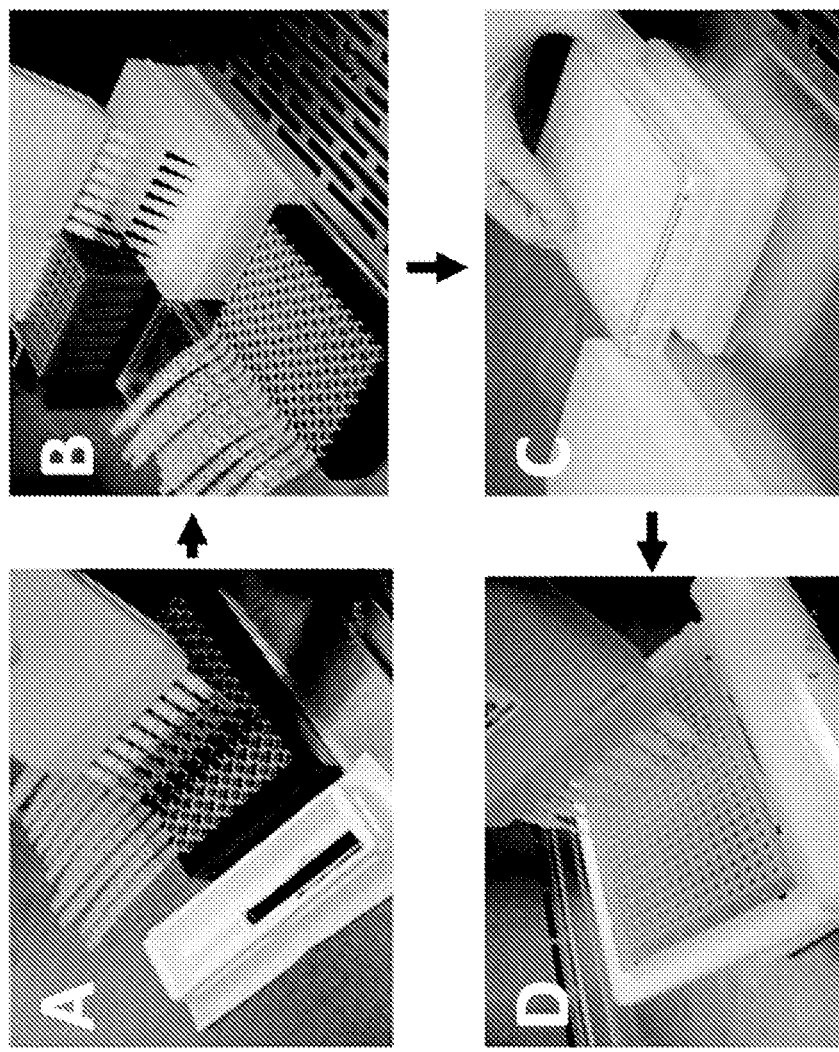

Institutional Review Board (IRB) approved heparinized blood samples were obtained from Apex Research (Tustin, Calif.). Sixty pi of whole blood was added into 8-well strip microtubes, where various stimulants and controls were previously dispensed (FIG. 7A). After cap was closed, these strips were incubated at 37° C. for 0-7 hours, then stored frozen at −80° C. Thawed blood was transferred to filterplate to trap leukocytes on membrane, then lysis buffer was added into each well (FIG. 7B). Lysate was transferred to oligo(dT)-immobilized microplate for poly(A)+ mRNA isolation, followed by cDNA synthesis on the same plate (FIG. 7C). The cDNA solution was transferred to 384-well plate for real time PCR using iTaqSYBR (Biorad, Hercules, Calif.) in a thermal cycler (PRISM 7900, ABI) (FIG. 7D). PCR condition was 95° C. for 10 min followed by 50 cycles of 65° C. for 1 min and 95° C. for 30 sec. The melting curve was always analyzed to confirm that PCR signals were derived from a single PCR product. The cycle threshold (Ct) was determined by analytical software (SDS, ABI), and statistical p values were calculated by t-test using 3 Ct values each of stimulant and control. The Ct of drug-treated triplicate samples were subtracted individually by the mean Ct values of control samples to calculate ΔCt, and the fold increase was calculated as $2^{(-\Delta Ct)}$.

In Vivo

Research protocol was approved by IRB (Cleveland Clinic). Blood was drawn into PAXgene tubes from patients before and after INF therapy. Total RNA was extracted from nucleated cells and poly(A)+ RNA was further isolated in using oligo(dT)-immobilized microplate, followed by RT-PCR as shown in the ex vivo assay. To normalize the data, Ct value of each mRNA was subtracted by the Ct value of ACTB to calculate ΔCt, and % ACTB was determined as $2^{(-\Delta t)} \times 100$.

Results

Figure 8:
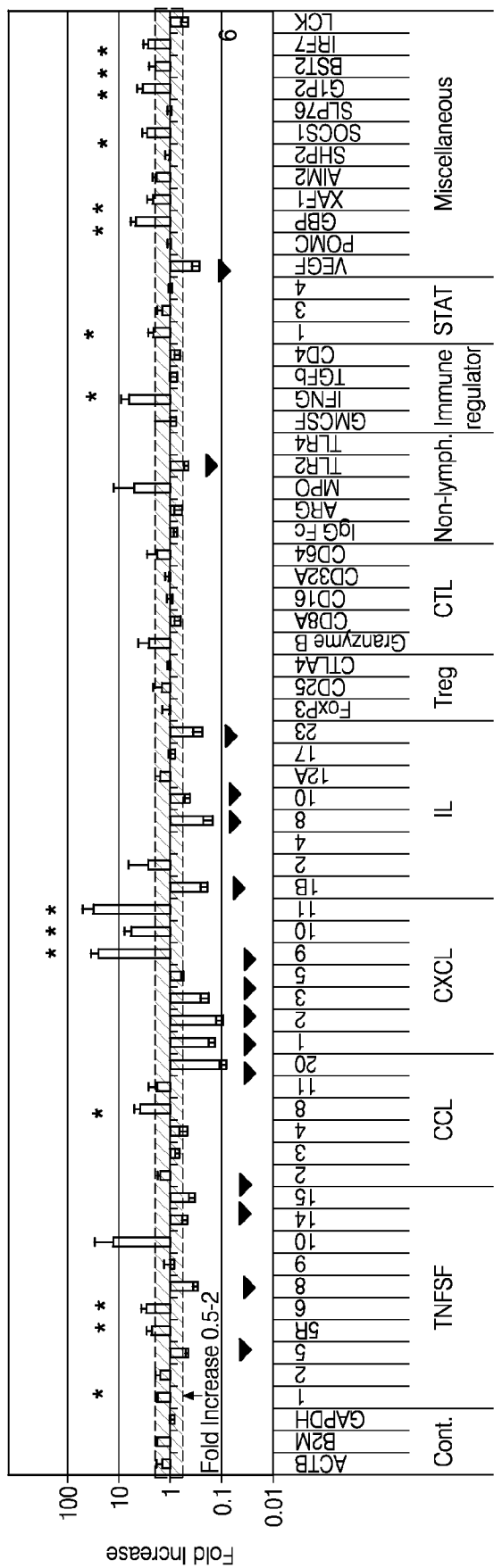
FIG. 8. Results of ex vivo mRNA screening.
Figure 9F:
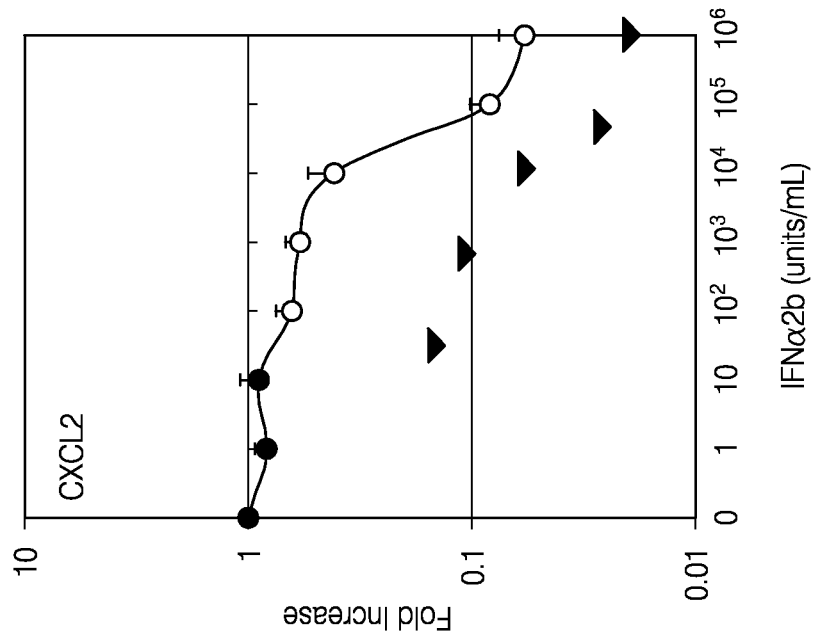
Figure 9E:
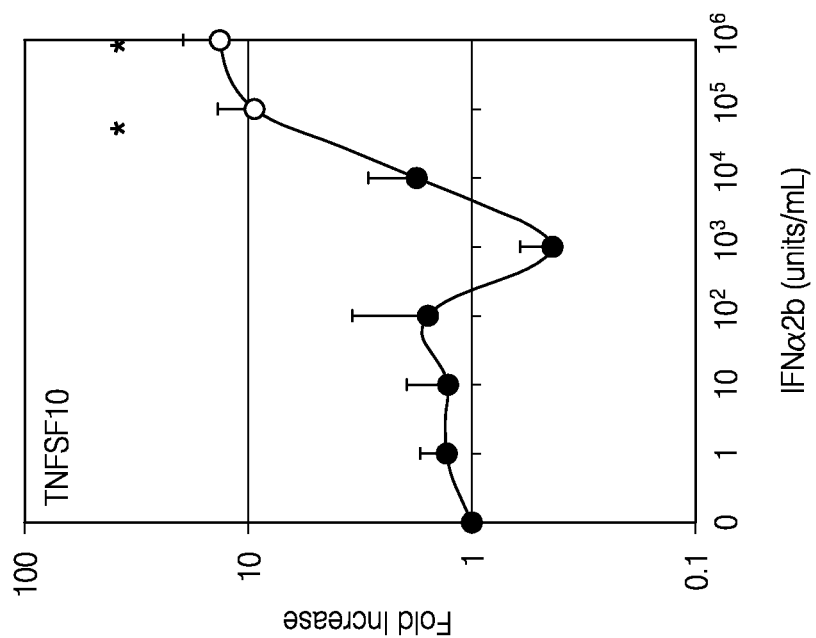
Figure 9H:
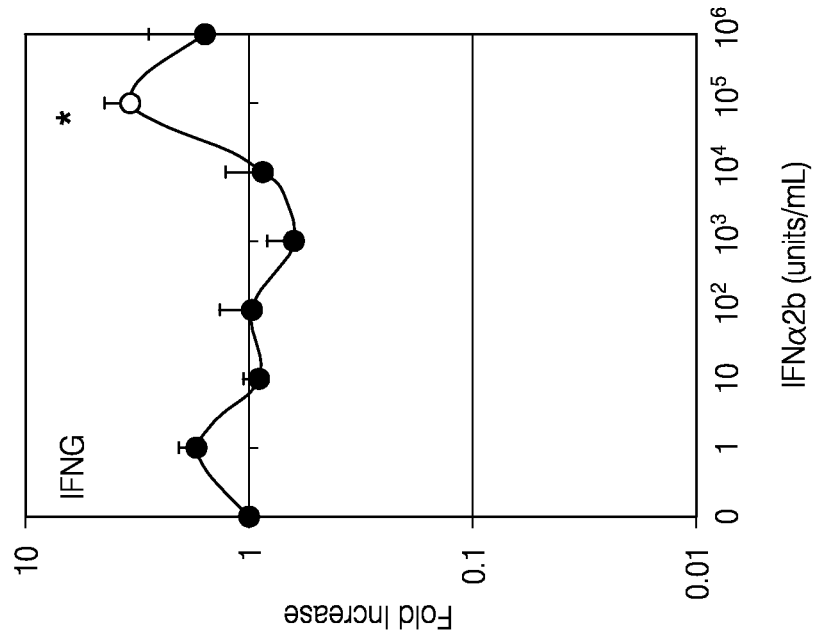
Figure 9G:
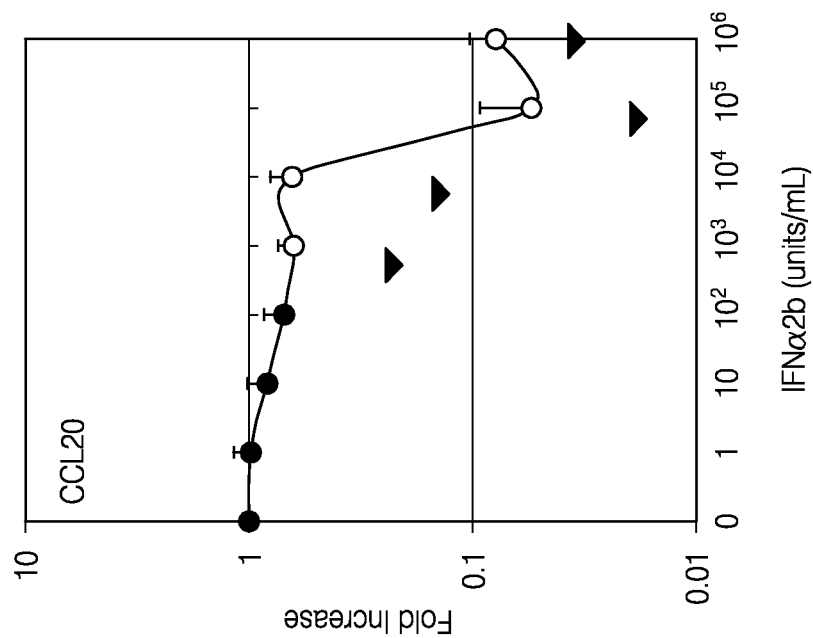
Figure 10B:
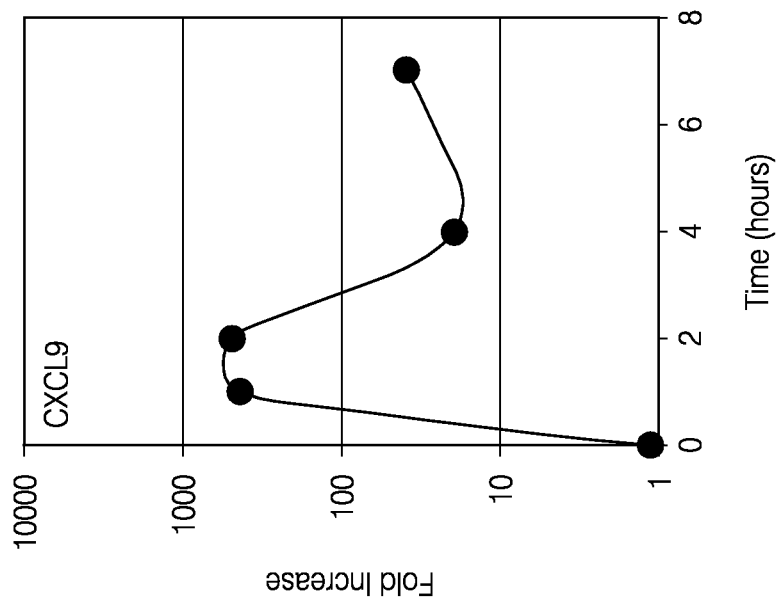
FIGS. 10A-10H. Ex vivo dose kinetic relationship between various mRNA expression and IFNα-2b stimulation FIG. 11. Identification of Responder and Non-responder Patients based on mRNA expression.
Figure 10A:
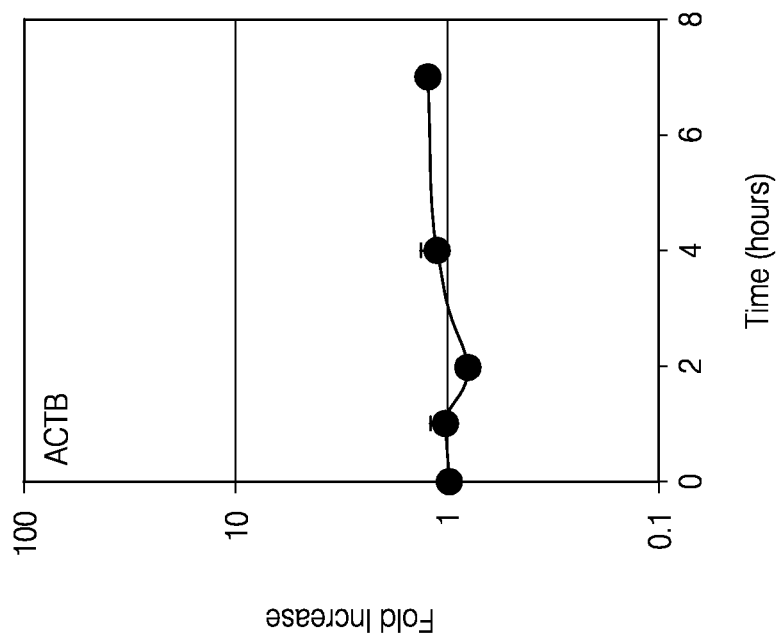
Figure 10D:
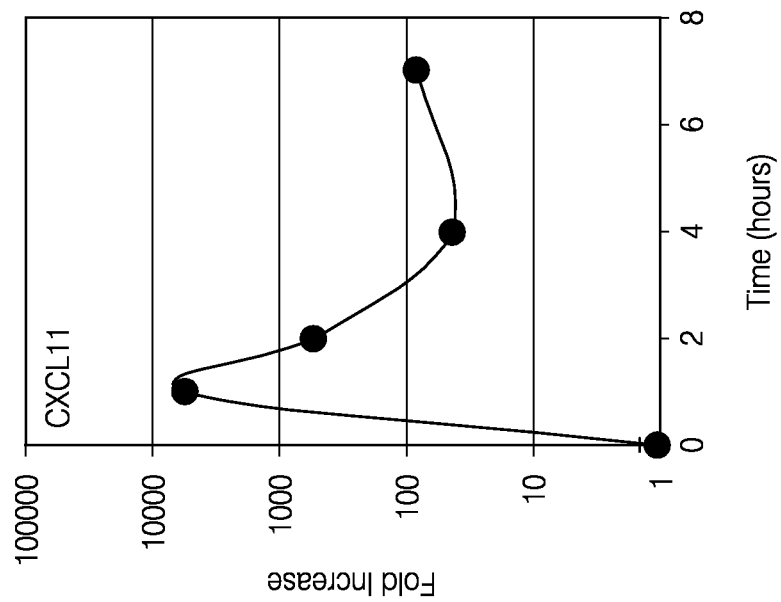
Figure 10C:
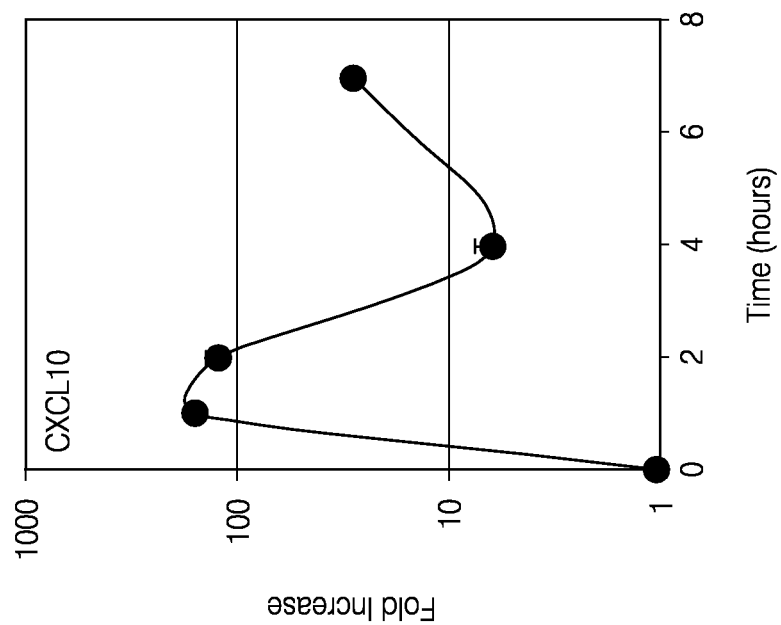
Figure 10F:
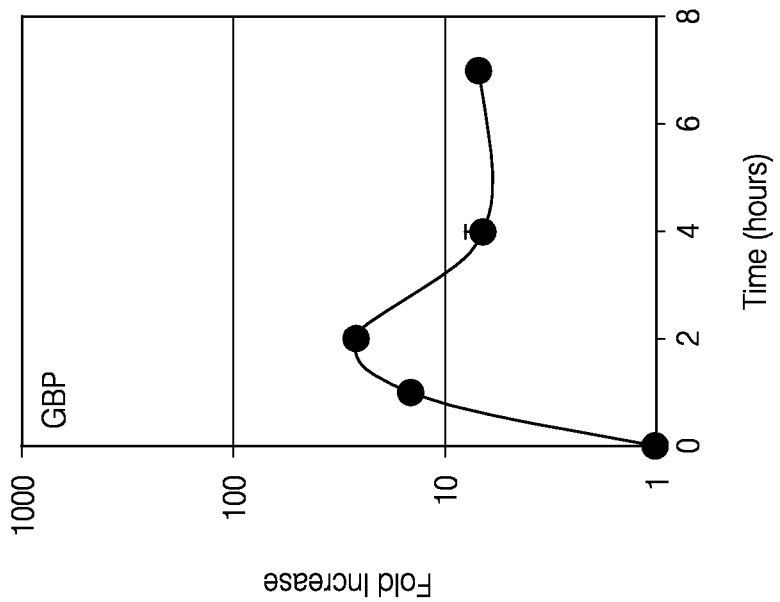
Figure 10E:
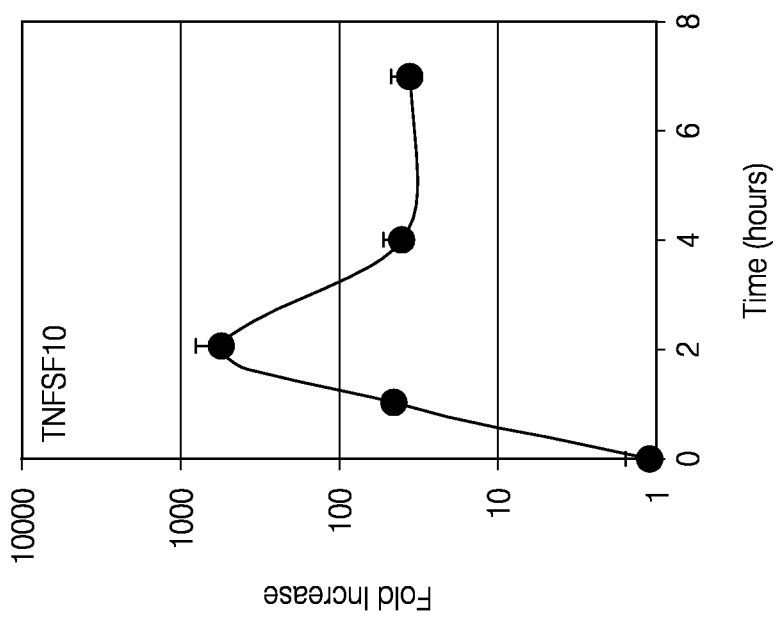
Figure 10H:
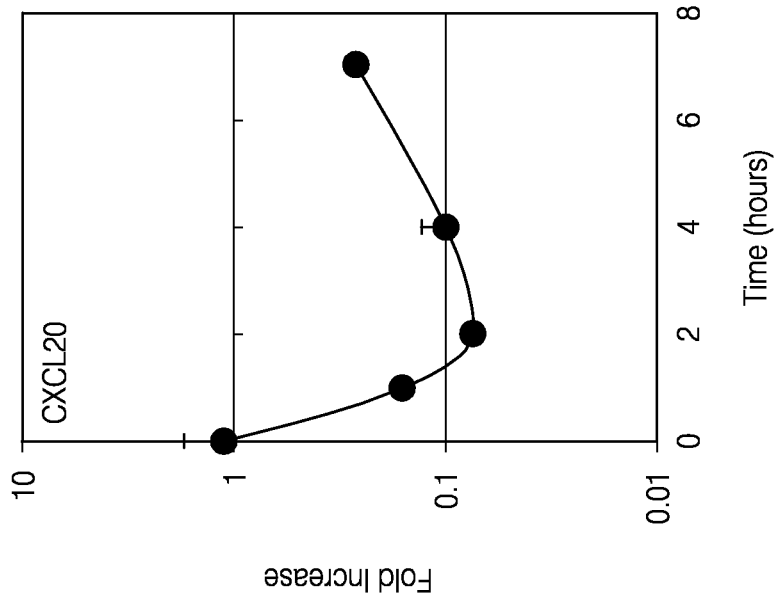
Figure 10G:
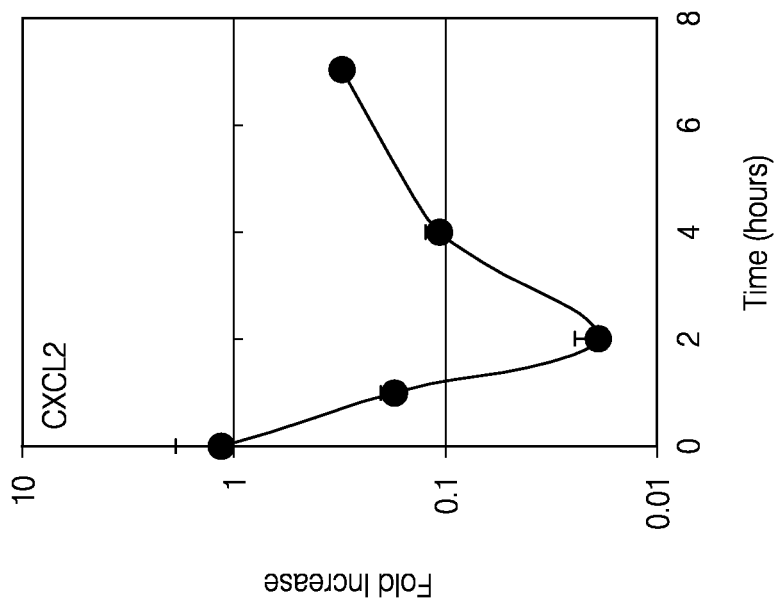

Whole blood was stimulated with PBS or INFa2b (final concentration: 105 units/mL) at 37° C. for 4 hours, then various mRNAs were quantified as described in the Methods. The fold increase of 3 control genes (ACTB, B2M, and GAPDH) were all between 0.5-2.0. Statistically significant induction (yellow bars, also identified by an "*") were identified for TNFSF1, 6, TNFRSR5, CCL8, CXCL9, 10, 11, IFNG, STAT1, GBP, XAF1, SOCS1, G1P2, BST2, and IRF7, whereas significant reduction (green bars, also identified by an "▼") was identified for TNFSF5, 8, 14, 15, CCL20, CXCL1, 2, 3, 5, IL1B, 8, 10, 23, TRL2, VEGF, and LCK. See FIG. 8.

Both IFNα2b-induced increase (CXCL9, 10, 11, TNFSF10, GBP) and decrease (CXCL2 and CCL20) of mRNA were similarly dose dependent with the peak at $10^5$ units/mL ACTB was not changed by INFα2b stimulation. Incubation was 4 hours. See FIG. 9.

Both IFNα2b-induced increase (CXCL9, 10, 11, TNFSF10, GBP) and decrease (CXCL2 and CCL20) of mRNA happened rapidly with a peak around 1-2 hours, with subsequent plateau phase for at least 7 hours. $10^5$ units/mL INFα2b was used. See FIG. 10.

Figure 11:
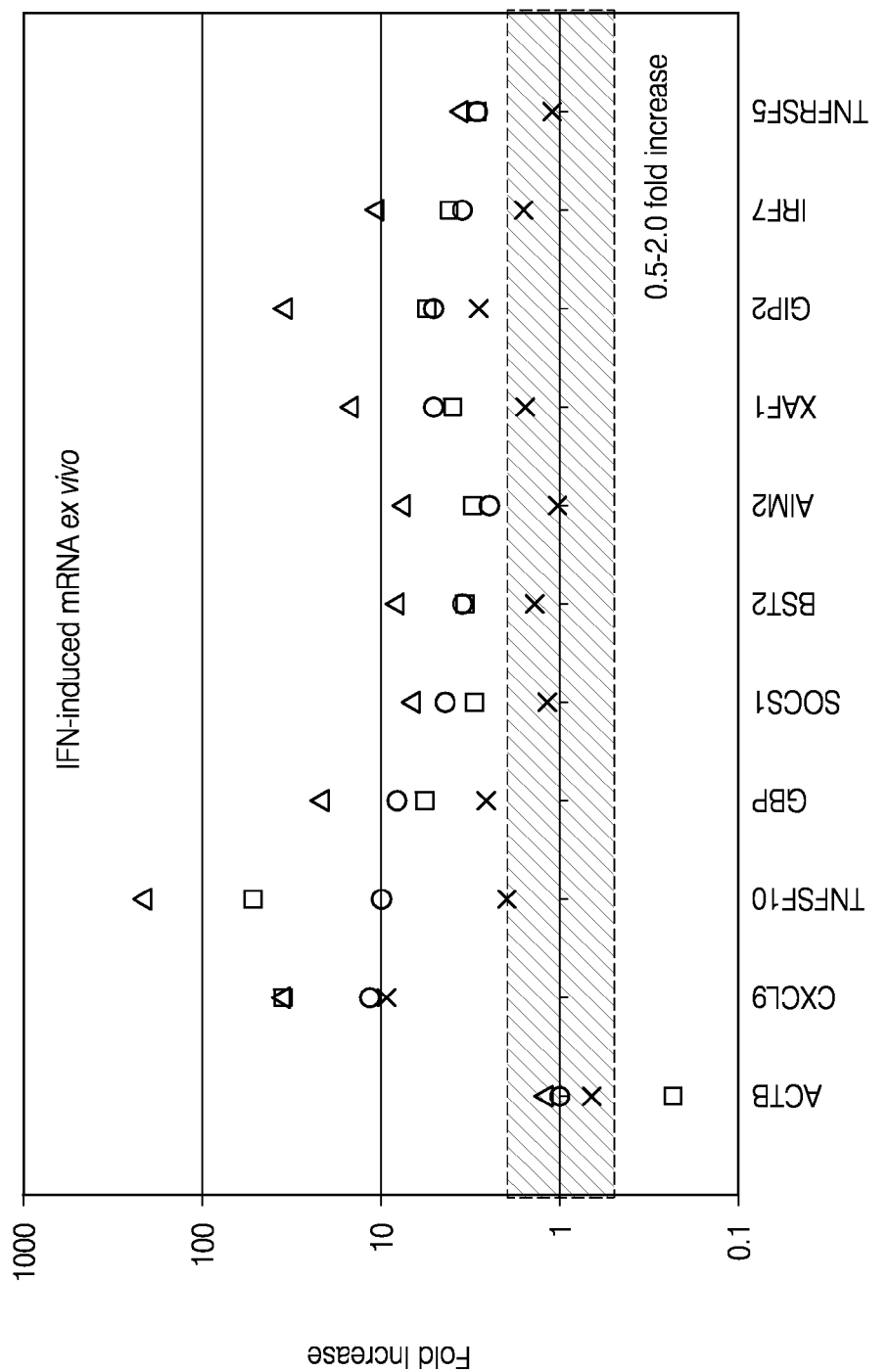
Figure 12A:
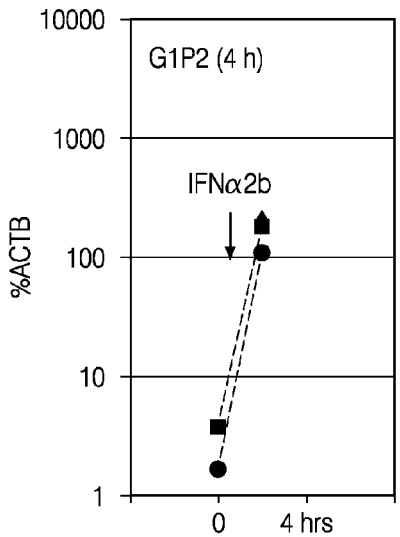
FIGS. 12A-12T. In vivo induction of various mRNA by IFNα-2b administration.
Figure 12B:
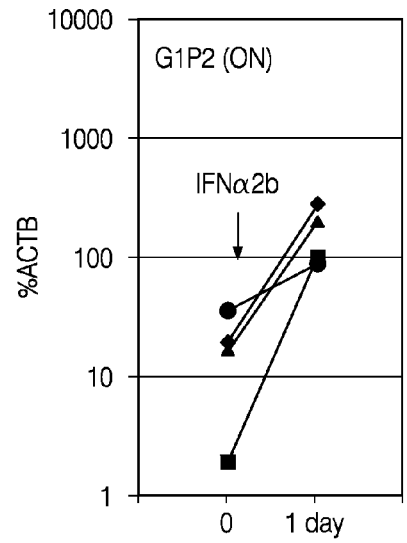
Figure 12C:
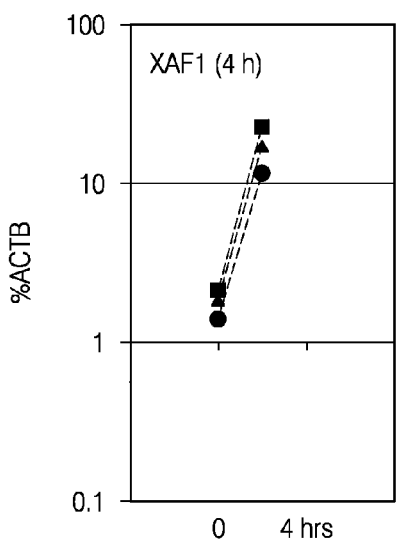
Figure 12D:
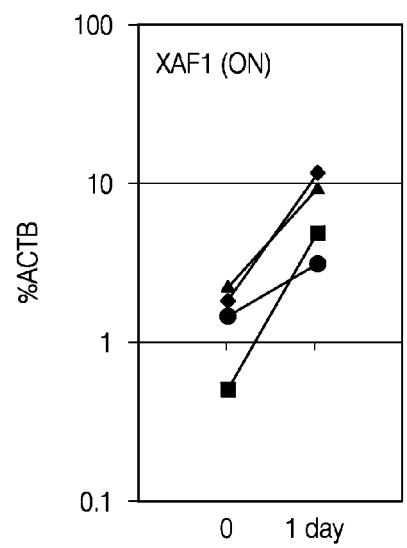
Figure 12E:
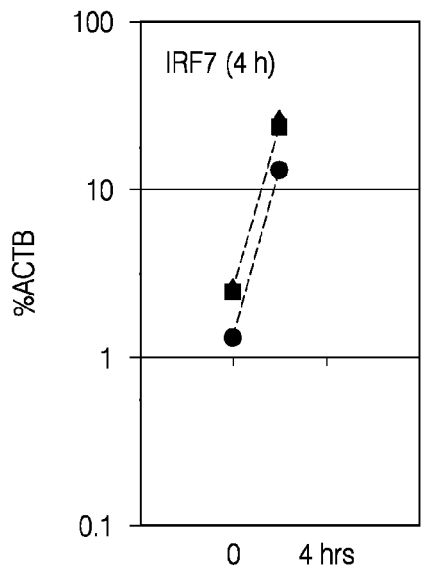
Figure 12F:
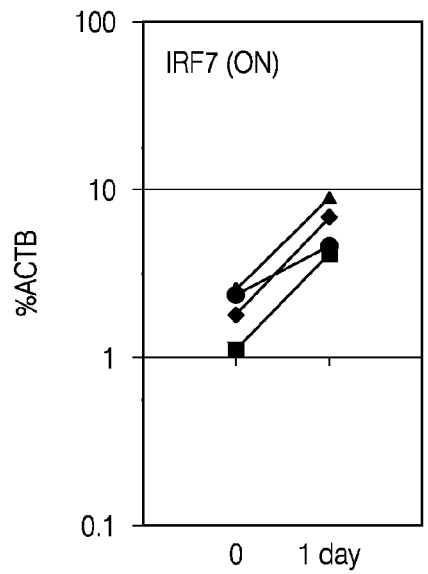
Figure 12G:
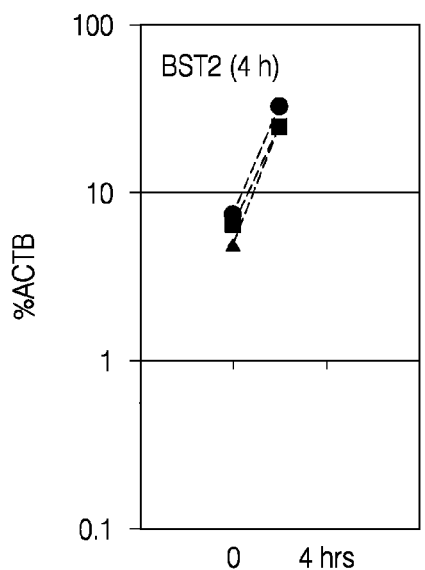
Figure 12H:
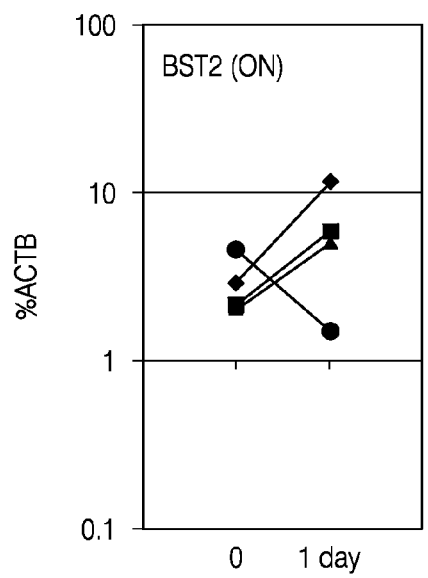
Figure 12I:
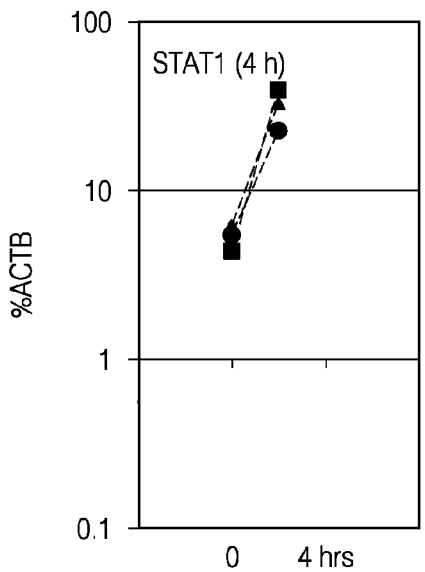
Figure 12J:
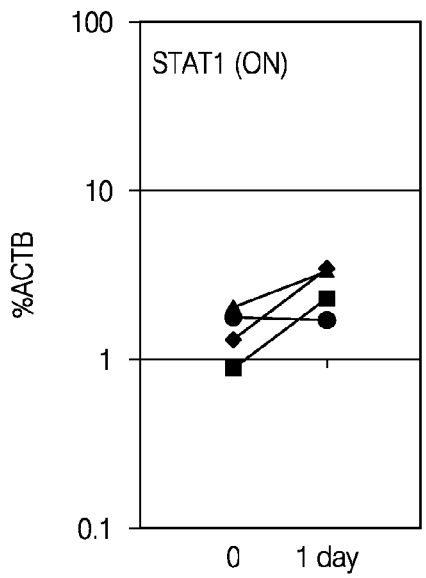
Figure 12K:
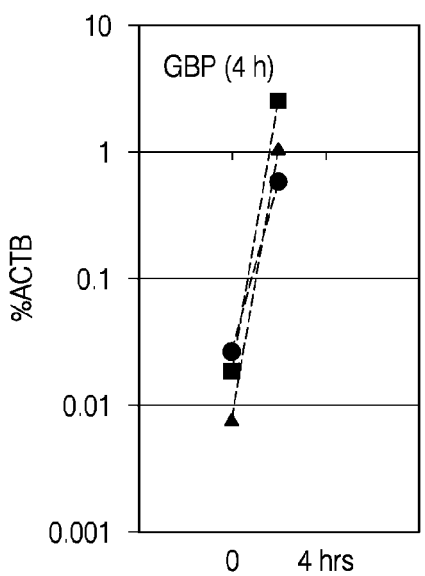
Figure 12L:
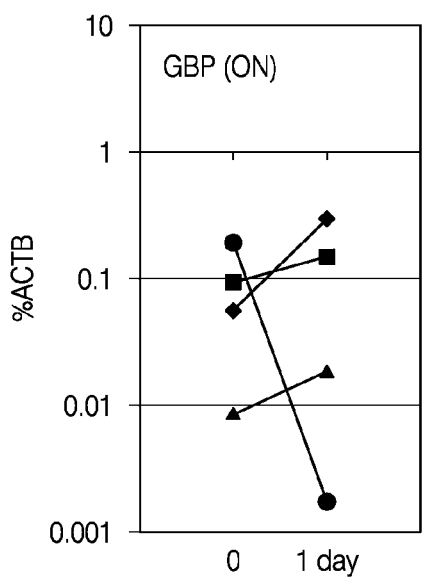
Figure 12M:
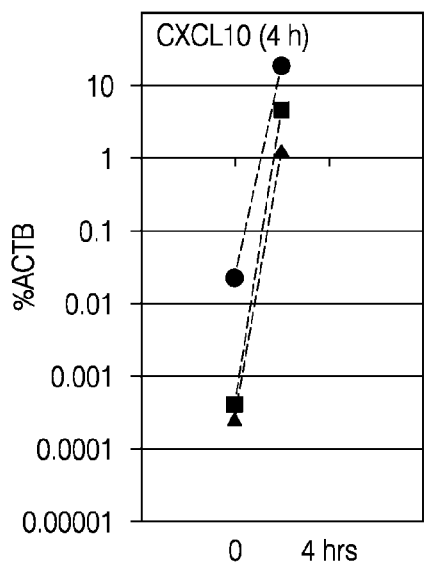
Figure 12N:
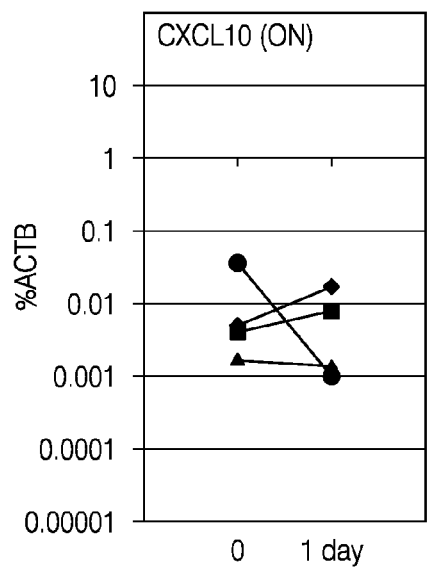
Figure 12O:
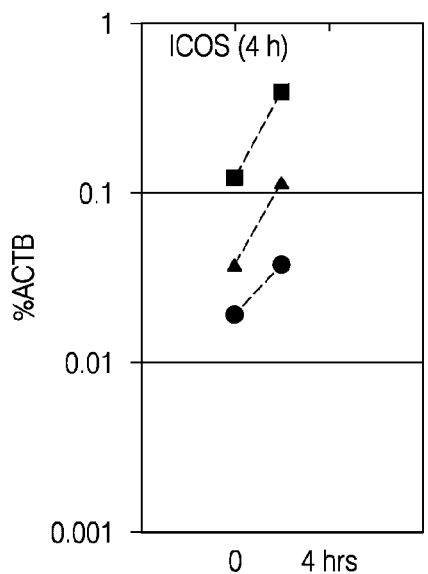
Figure 12P:
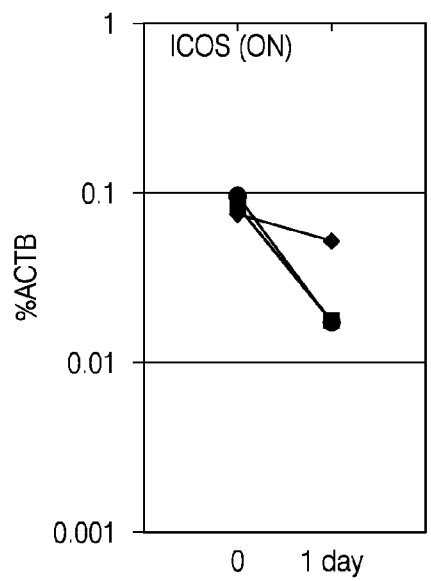
Figure 12Q:
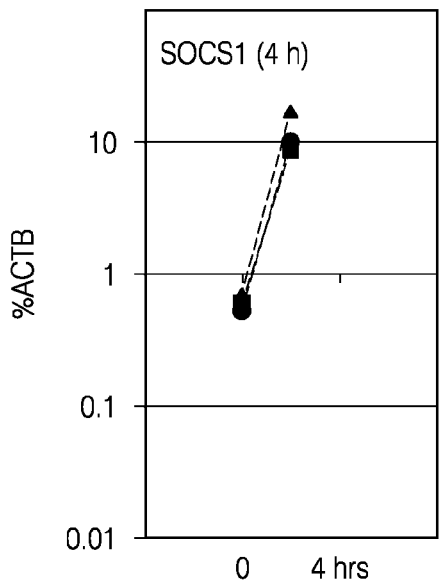
Figure 12R:
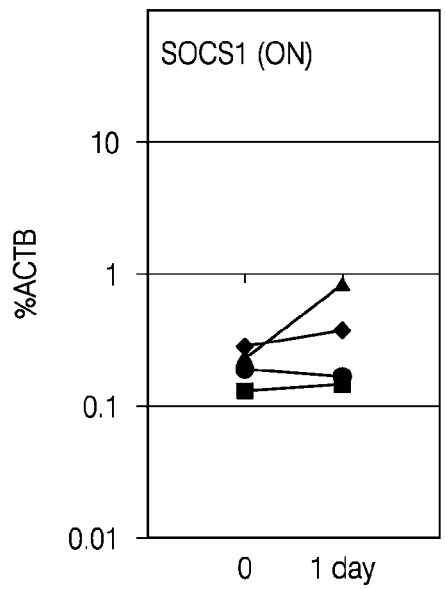
Figure 12S:
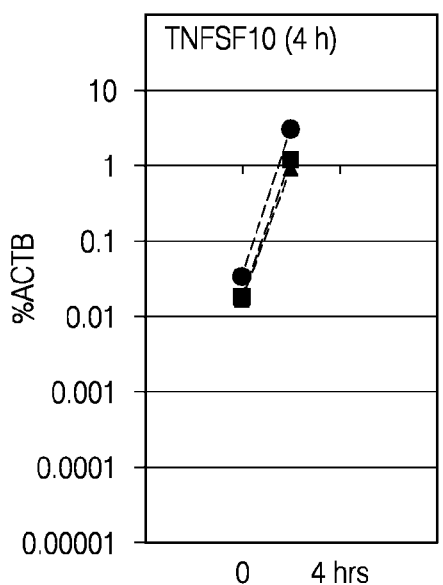
Figure 12T:
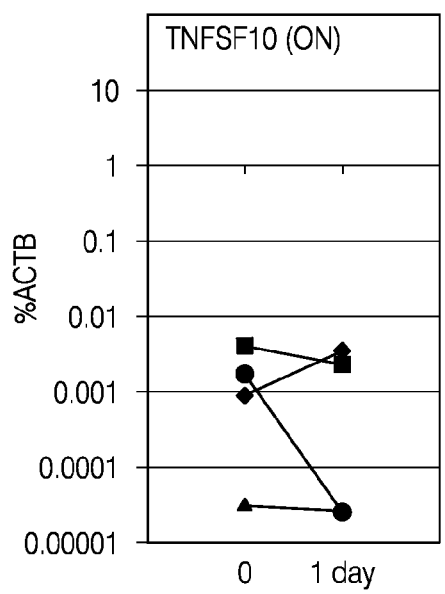

Blood samples from 4 adult volunteers were tested for ex vivo induction of mRNAs using $10^5$ units/mL of IFNα2b. One individual (X) failed to show IFNα2b-induced TNFSF10, SOCS1, BST2, AIM2, XAF1, IRF7, and TNFRSF5, although CXCL9, GBP and G1P2 were induced. See FIG. 11.

Blood was drawn before and 4 hours (4 h) (n=3) or overnight (ON) (n=4) after INFa2b injection, and various mRNAs were quantified, and expressed as % ACTB. The levels of STAT1, IRF7, XAF1, and G1P2 mRNAs were high for both 4 h and ON, whereas the increase of TNFSF10, CXCL10, SOCS1 and ICOS was transient. One patient showed the decrease of GBP, BST2, TNFSF10 and CXCL10 at ON. See FIG. 12.

Figure 13A:
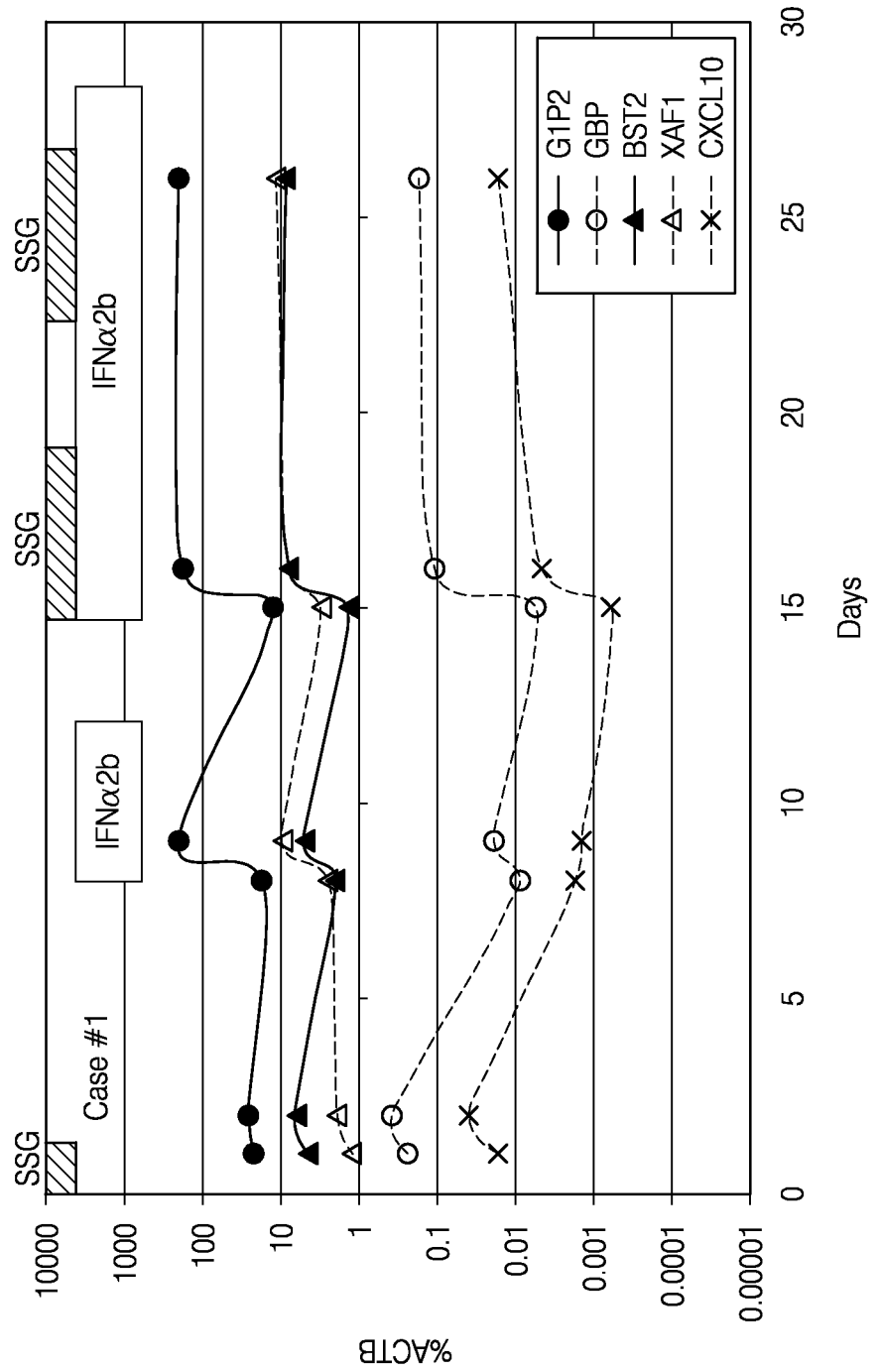
FIGS. 13A-13B. Monitoring of clinical course (in vivo)
Figure 13B:
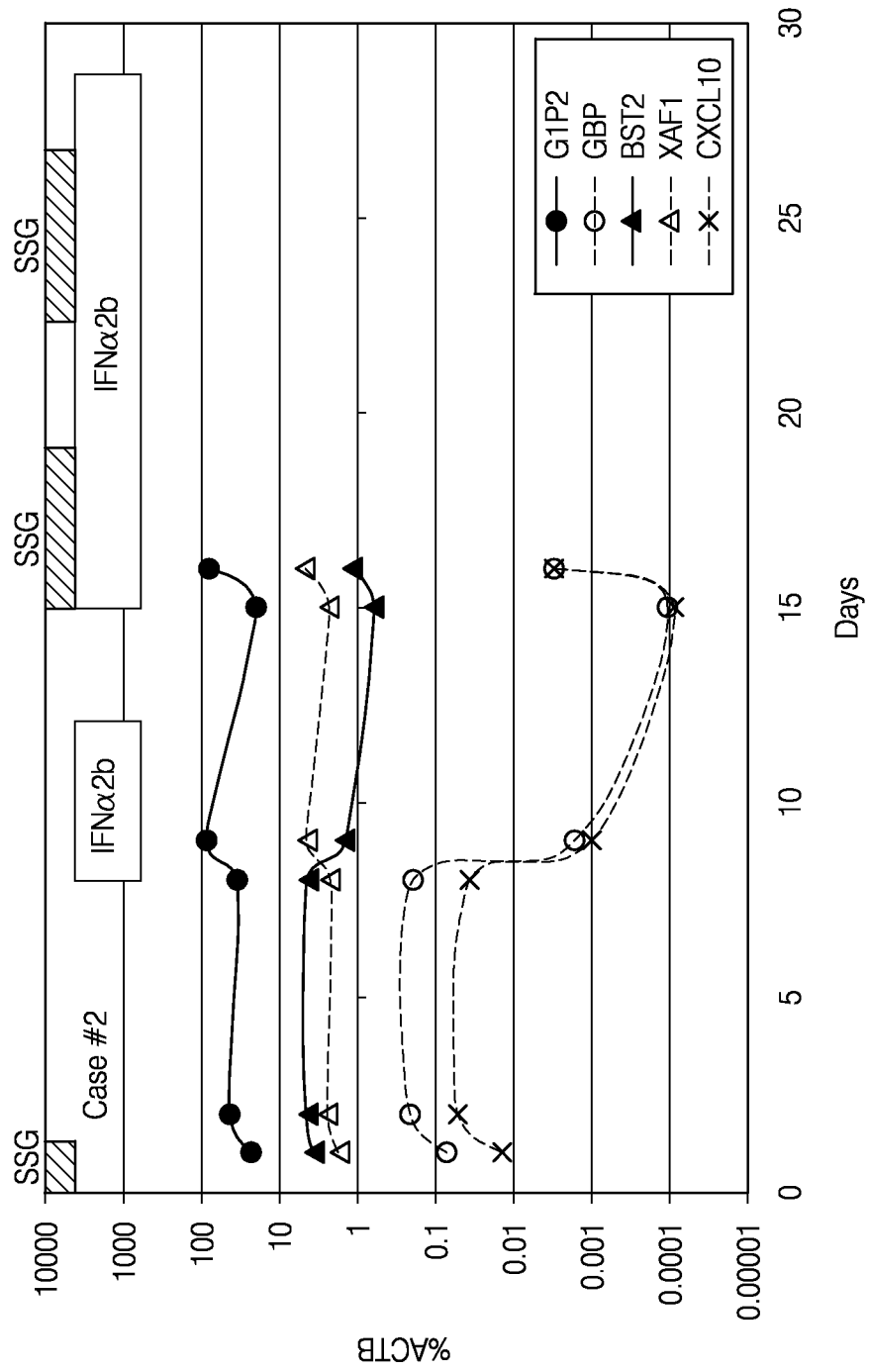

IFNα2b (3×106 units/m2) was injected S.C. at Day 8-12, and Day 15-28. At Day 1, Day 15-19, and Day 22-26, sodium stibo-gluconate (SSG) (400 mg/m2/day) was given I.V. Blood was drawn before and 4 hours after IFNα2b/SSG injection at Day 1, 8, 15, and Day 26 (Case #1), and various mRNAs were quantified and expressed as % ACTB. In Case #1, induction of G1P2, GBP, BST2, and XAF1 were observed for both 1st (Day 8) and 2nd (Day 15) series of IFNα2b treatment. CXCL10 was not induced at 1st treatment, but induced at 2nd treatment. During treatment period (Day 15-28), the levels of these mRNA were maintained high. In Case #2, the levels of BST2, GBP, and CXCL10 were decreased at 1st treatment, whereas all 5 mRNAs were induced at 2nd treatment. See, e.g., FIGS. 13A and 13B.

PRELIMINARY CONCLUSION

Various mRNA were induced in whole blood leukocytes after IFNα2b treatment in both ex vivo and in vivo, and such mRNA induction was successfully detected by RT-PCR.

The action of IFNα2b was very rapid in both ex vivo (1-2 hours) (FIG. 10) and in vivo (4 hours) (FIG. 12).

The action of IFNα2b was not observed universally among all tested individuals, and substantial individual-to-individual variation, or responders/non-responders were identified (BST2, GBP, TNFSF10, and CXCL10 in FIGS. 11-13). mRNA with such variation possibly identifying candidate markers for personalized medicine diagnostics in the future.

TABLE 2

Correlation of ex vivo and in vivo expression changes in response to IFNα-2b

| mRNA | in vivo Pt. #1 | in vivo Pt. #2 | ex vivo |
|---|---|---|---|
| Induced: | | | |
| CCL8 | ↑ | ↑ | ↑ |
| CXCL9 | ↑ | ↑ | ↑ |
| CXCL10 | ↑ | ↑ | ↑ |
| CXCL11 | ↑ | ↑ | ↑ |
| GBP | ↑ | ↑ | ↑ |
| XAF1 | ↑ | ↑ | ↑ |
| SOCS1 | ↑ | ↑ | ↑ |
| G1P2 | ↑ | ↑ | ↑ |
| BST2 | ↑ | ↑ | ↑ |
| IRF7 | ↑ | ↑ | ↑ |
| Reduced: | | | |
| TNFSF5 | ↓ | ↓ | ↓ |
| IL8 | ↓ | ↓ | ↓ |
| IL23 | ↓ | ↓ | ↓ |
| Preliminary Data: | | | |
| TNFSF10 | — | ↑ | ↑ |
| TNFRSF5 | ↑ | — | ↑ |
| TNFSF6 | — | — | ↑ |
| TNFSF8 | — | — | ↑ |
| TNFSF15 | — | — | ↓ |
| CCL20 | — | ↓ | ↓ |
| CXCL1 | — | — | ↓ |
| CXCL2 | — | — | ↓ |
| CXCL3 | — | — | ↓ |
| CXCL5 | — | ↑ | ↓ |
| IL1B | — | ↑ | ↓ |
| INFg | ↓ | n.d. | ↑ |
| VEGF | — | — | ↓ |
| AIM2 | ↑ | ↑ | — |

What is claimed is:

1. A method for treating a subject having hepatitis with an interferon-based therapy, the method comprising:
   (A) having at least a first and second sample of whole blood from said subject sent to a laboratory prior to interferon administration, for the laboratory to perform an assay comprising the following steps (1)-(4):
      (1) exposing said first sample of whole blood from said subject to interferon alpha 2b in a solvent for an amount of time sufficient for said interferon alpha 2b to alter the expression of one or more markers whose expression is potentially altered in response to exposure to IFN alpha 2b selected from the group consisting of TNFSF10, CXCL10, GBP, and BST2;
      (2) exposing said second sample of whole blood from said subject to the solvent without said interferon alpha 2b for said amount of time;
      (3) quantifying the effect of said interferon alpha 2b as a change in expression of said one or more markers by a method comprising:
         (i) isolating mRNA from said first whole blood sample,
         (ii) contacting said mRNA from said first whole blood sample with a reverse transcriptase to generate a stimulated complementary DNA (cDNA), and
         (iii) contacting said stimulated cDNA with sense and antisense primers that are specific for said one or more markers and a DNA polymerase to generate stimulated amplified DNA; and
         (iv) isolating mRNA from said second whole blood sample,
         (v) contacting said mRNA from said second whole blood sample with a reverse transcriptase to generate control complementary DNA (cDNA), and
         (vi) contacting said control cDNA with sense and antisense primers that are specific for said one or more markers and a DNA polymerase to generate control amplified DNA;
      (4) calculating a change in the amount of marker mRNA in said first whole blood sample compared to the amount of marker mRNA in said second whole blood sample;
   (B) treating the subject with an interferon-based therapy if the results of said assay indicate there is a difference in the amount of marker mRNA quantified from said first blood sample as compared to said second blood sample.

2. The method of claim 1, wherein said one or more markers comprise a marker that increases in response to interferon alpha 2b.

3. The method of claim 1, wherein said one or more markers comprise a marker that decreases in response to interferon alpha 2b.

4. The method of claim 1, wherein said interferon alpha 2b is present in a concentration from about 1 to about 100,000 units per mL.

5. The method of claim 1, wherein said exposing is for a time between one hour and seven hours and wherein said exposing occurs at about thirty-seven (37) degrees Celsius.

6. The method of claim 1, wherein said whole blood comprises human blood that is optionally heparinzed.

7. The method of claim 1, wherein said hepatitis is caused by the hepatitis B virus or the hepatitis C virus.

8. The method of claim 1, wherein a medical professional administers the recommended interferon-based therapy.

9. A method for treating a subject having hepatitis with interferon therapy based on the ongoing efficacy of the interferon therapy, the method comprising:
   having a first sample of whole blood collected from said subject prior to interferon alpha 2b administration sent to a laboratory;
   having a second sample of whole blood collected from said subject after interferon alpha 2b administration sent to a laboratory, for the laboratory to perform an assay comprising the following steps (1)-(2):
      (1) quantifying the effect of one or more markers whose expression is potentially altered in response to exposure to IFN2 alpha b selected from the group consisting of TNFSF10, CXCL10, GBP, and BST2 by a method comprising:
         (i) isolating mRNA from said first whole blood sample,
         (ii) contacting said mRNA from said first whole blood sample with a reverse transcriptase to generate a first complementary DNA (cDNA), and
         (iii) contacting said first cDNA with sense and antisense primers that are specific for said one or more markers and a DNA polymerase to generate a first amplified DNA; and (iv) isolating mRNA from said second whole blood sample,
(v) contacting said mRNA from said second whole blood sample with a reverse transcriptase to generate a second complementary DNA (cDNA), and
(vi) contacting said second cDNA with sense and antisense primers that are specific for said one or more markers and a DNA polymerase to generate a second amplified DNA;

(2) determining the efficacy of interferon alpha 2b therapy by comparing the expression of said one or more markers in said first whole blood sample and in said second whole blood sample by comparing the amount of said first and said second amplified DNA; and (I) continuing said interferon alpha 2b therapy based on the efficacy of the therapy, said efficacy being indicated by a difference in the amount of marker mRNA quantified from said second blood sample as compared to said first blood sample in results from said assay; or (II) discontinuing said interferon therapy based on a lack of efficacy of the therapy, said lack of efficacy being indicated by a lack of difference in the amount of marker mRNA quantified from said second blood sample as compared to said first blood sample in results from said assay.

10. The method of claim 9, wherein said hepatitis is hepatitis B virus or hepatitis C virus.

11. The method of claim 1, further comprising comparing said difference by comparing to a normal effect of interferon expression of said one or more markers, wherein said normal effect is calculated as an average change in expression levels of said one or more markers in a panel of control individuals.

12. The method of claim 1, wherein said difference is a statistically significant difference.

* * * * *

SEQUENCE LISTING

```
<160> NUMBER OF SEQ ID NOS: 132

<210> SEQ ID NO 1
<211> LENGTH: 18
<212> TYPE: DNA
<213> ORGANISM: Homo sapiens
<220> FEATURE:
<221> NAME/KEY: misc_feature
<223> OTHER INFORMATION: Sense Primer for beta-actin

<400> SEQUENCE: 1
cctggcaccc agcacaat                                                 18

<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for beta-actin

<400> SEQUENCE: 2
gccgatccac acggagtact                                               20

<210> SEQ ID NO 3
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for beta-2 microglobulin
```

<400> SEQUENCE: 3
tgactttgtc acagcccaag ata                                          23

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for beta-2 microglobulin

<400> SEQUENCE: 4
aatgcggcat cttcaaacct                                              20

<210> SEQ ID NO 5
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for GAPDH

<400> SEQUENCE: 5
aaggactcat gaccacagtc cat                                          23

<210> SEQ ID NO 6
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for GAPDH

<400> SEQUENCE: 6
ccatcacgcc acagtttcc                                               19

<210> SEQ ID NO 7
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for TNFSF1

<400> SEQUENCE: 7
cagctatcca cccacacaga tg                                           22

<210> SEQ ID NO 8
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for TNFSF1

<400> SEQUENCE: 8
cgaaggctcc aaagaagaca gt                                           22

<210> SEQ ID NO 9
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for TNFSF2

<400> SEQUENCE: 9
cgaaggctcc aaagaagaca gt                                          22

<210> SEQ ID NO 10
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for TNFSF2

<400> SEQUENCE: 10
cagggcaatg atcccaaagt                                             20

<210> SEQ ID NO 11
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for TNFSF5

<400> SEQUENCE: 11
ccacagttcc gccaaacct                                              19

<210> SEQ ID NO 12
<211> LENGTH: 24
<212> TYPE: DNA
<213> ORGANISM: Homo sapiens
<220> FEATURE:
<221> NAME/KEY: misc_feature
<223> OTHER INFORMATION: Antisense primer for TNFSF5

<400> SEQUENCE: 12
cacctggttg caattcaaat actc                                        24

<210> SEQ ID NO 13
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for TNFRSF1

<400> SEQUENCE: 13
ggccaagaag ccaaccaata                                             20

<210> SEQ ID NO 14
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for TNFRSF5

<400> SEQUENCE: 14
gaagatcgtc gggaaaattg at                                          22

<210> SEQ ID NO 15
<211> LENGTH: 24
<212> TYPE: DNA
<213> ORGANISM: Homo sapiens
<220> FEATURE:
<221> NAME/KEY: misc_feature
<223> OTHER INFORMATION: Sense primer for TNFSF6

<400> SEQUENCE: 15

-continued tggcagcatc ttcacttcta aatg                                                        24

<210> SEQ ID NO 16
<211> LENGTH: 24
<212> TYPE: DNA
<213> ORGANISM: Homo sapiens
<220> FEATURE:
<221> NAME/KEY: misc_feature
<223> OTHER INFORMATION: Antisense primer for TNFSF6

<400> SEQUENCE: 16
gaaatgagtc cccaaaacat ctct                                                        24

<210> SEQ ID NO 17
<211> LENGTH: 24
<212> TYPE: DNA
<213> ORGANISM: Homo sapiens
<220> FEATURE:
<221> NAME/KEY: misc_feature
<223> OTHER INFORMATION: Sense primer for TNFSF8

<400> SEQUENCE: 17
accaccatat cagtcaatgt ggat                                                        24

<210> SEQ ID NO 18
<211> LENGTH: 25
<212> TYPE: DNA
<213> ORGANISM: Homo sapiens
<220> FEATURE:
<221> NAME/KEY: misc_feature
<223> OTHER INFORMATION: Antisense primer for TNFSF8

<400> SEQUENCE: 18
gaagatggac aacacattct caaga                                                       25

<210> SEQ ID NO 19
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for TNFSF9

<400> SEQUENCE: 19
agctacaaag aggacacgaa gga                                                         23

<210> SEQ ID NO 20
<211> LENGTH: 24
<212> TYPE: DNA
<213> ORGANISM: Homo sapiens
<220> FEATURE:
<221> NAME/KEY: misc_feature
<223> OTHER INFORMATION: Antisense primer for TNFSF9

<400> SEQUENCE: 20
cgcagctcta gttgaaagaa gaca                                                        24

<210> SEQ ID NO 21
<211> LENGTH: 26
<212> TYPE: DNA
<213> ORGANISM: Homo sapiens
<220> FEATURE:
<221> NAME/KEY: misc_feature
<223> OTHER INFORMATION: Sense primer for TNFSF10

<400> SEQUENCE: 21 gggaatatttt gagcttaagg aaaatg                                        26

<210> SEQ ID NO 22
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for TNFSF10

<400> SEQUENCE: 22
aaaaggcccc gaaaaaactg                                                20

<210> SEQ ID NO 23
<211> LENGTH: 18
<212> TYPE: DNA
<213> ORGANISM: Homo sapiens
<220> FEATURE:
<221> NAME/KEY: misc_feature
<223> OTHER INFORMATION: Sense primer for TNFSF4

<400> SEQUENCE: 23
cgtccgtgtg ctggatga                                                  18

<210> SEQ ID NO 24
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for TNFSF14

<400> SEQUENCE: 24
catgaaagcc ccgaagtaag ac                                             22

<210> SEQ ID NO 25
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for TNFSF15

<400> SEQUENCE: 25
tgcgaagtag gtagcaactg gtt                                            23

<210> SEQ ID NO 26
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for TNFSF15

<400> SEQUENCE: 26
ccattagctt gtccccttct tg                                             22

<210> SEQ ID NO 27
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for CCL2

<400> SEQUENCE: 27
ccattgtggc caaggagatc                                                20

```
<210> SEQ ID NO 28
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for CCL2

<400> SEQUENCE: 28
tgtccaggtg gtccatgga                                                    19

<210> SEQ ID NO 29
<211> LENGTH: 28
<212> TYPE: DNA
<213> ORGANISM: Homo sapiens
<220> FEATURE:
<221> NAME/KEY: misc_feature
<223> OTHER INFORMATION: Sense primer for CCL3

<400> SEQUENCE: 29
cacagaattt catagctgac tactttga                                          28

<210> SEQ ID NO 30
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for CCL3

<400> SEQUENCE: 30
tcgcttggtt aggaagatga ca                                                22

<210> SEQ ID NO 31
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for CCL4

<400> SEQUENCE: 31
ggtattccaa accaaaagaa gca                                               23

<210> SEQ ID NO 32
<211> LENGTH: 26
<212> TYPE: DNA
<213> ORGANISM: Homo sapiens
<220> FEATURE:
<221> NAME/KEY: misc_feature
<223> OTHER INFORMATION: Antisense primer for CCL4

<400> SEQUENCE: 32
gttcagttcc aggtcataca cgtact                                            26

<210> SEQ ID NO 33
<211> LENGTH: 26
<212> TYPE: DNA
<213> ORGANISM: Homo sapiens
<220> FEATURE:
<221> NAME/KEY: misc_feature
<223> OTHER INFORMATION: Sense primer for CCL8

<400> SEQUENCE: 33
agagctacac aagaatcacc aacatc                                            26
```

<210> SEQ ID NO 34
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for CCL8

<400> SEQUENCE: 34
agacctcctt gccccgttt                                         19

<210> SEQ ID NO 35
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for CCL11

<400> SEQUENCE: 35
cccagaaagc tgtgatcttc aa                                     22

<210> SEQ ID NO 36
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for CCL11

<400> SEQUENCE: 36
tcctgcaccc acttcttctt g                                      21

<210> SEQ ID NO 37
<211> LENGTH: 28
<212> TYPE: DNA
<213> ORGANISM: Homo sapiens
<220> FEATURE:
<221> NAME/KEY: misc_feature
<223> OTHER INFORMATION: Sense primer for CCL20

<400> SEQUENCE: 37
gatacacaga ccgtattctt catcctaa                               28

<210> SEQ ID NO 38
<211> LENGTH: 26
<212> TYPE: DNA
<213> ORGANISM: Homo sapiens
<220> FEATURE:
<221> NAME/KEY: misc_feature
<223> OTHER INFORMATION: Antisense primer for CCL20

<400> SEQUENCE: 38
tgaaagatga tagcattgat gtcaca                                 26

<210> SEQ ID NO 39
<211> LENGTH: 16
<212> TYPE: DNA
<213> ORGANISM: Homo sapiens
<220> FEATURE:
<221> NAME/KEY: misc_feature
<223> OTHER INFORMATION: Sense primer for CXCL1

<400> SEQUENCE: 39
ccactgcgcc caaacc                                            16

```
<210> SEQ ID NO 40
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for CXCL1

<400> SEQUENCE: 40
gcaggattga ggcaagcttt                                           20

<210> SEQ ID NO 41
<211> LENGTH: 18
<212> TYPE: DNA
<213> ORGANISM: Homo sapiens
<220> FEATURE:
<221> NAME/KEY: misc_feature
<223> OTHER INFORMATION: Sense primer for CXCL2

<400> SEQUENCE: 41
cccctggcca ctgaactg                                             18

<210> SEQ ID NO 42
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for CXCL2

<400> SEQUENCE: 42
tggatgttct tgaggtgaat tcc                                       23

<210> SEQ ID NO 43
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for CXCL3

<400> SEQUENCE: 43
ggaattcacc tcaagaacat cca                                       23

<210> SEQ ID NO 44
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for CXCL5

<400> SEQUENCE: 44
gtggctatga cttcggtttg g                                         21

<210> SEQ ID NO 45
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for CXCL5

<400> SEQUENCE: 45
agagctgcgt tgcgtttgt                                            19

<210> SEQ ID NO 46
```

```
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for CXCL5

<400> SEQUENCE: 46
tggcgaacac ttgcagatta ct                                              22

<210> SEQ ID NO 47
<211> LENGTH: 25
<212> TYPE: DNA
<213> ORGANISM: Homo sapiens
<220> FEATURE:
<221> NAME/KEY: misc_feature
<223> OTHER INFORMATION: Sense primer for CXCL9

<400> SEQUENCE: 47
ccacctacaa tccttgaaag acctt                                           25

<210> SEQ ID NO 48
<211> LENGTH: 27
<212> TYPE: DNA
<213> ORGANISM: Homo sapiens
<220> FEATURE:
<221> NAME/KEY: misc_feature
<223> OTHER INFORMATION: Antisense primer for CXCL9

<400> SEQUENCE: 48
cagtgtagca atgatttcaa ttttctc                                         27

<210> SEQ ID NO 49
<211> LENGTH: 21
<212> TYPE: DNA
<213> ORGANISM: Homo sapiens
<220> FEATURE:
<221> NAME/KEY: misc_feature
<223> OTHER INFORMATION: Sense primer for CXCL10

<400> SEQUENCE: 49
tccacgtgtt gagatcattg c                                               21

<210> SEQ ID NO 50
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for CXCL10

<400> SEQUENCE: 50
tcttgatggc cttcgattct g                                               21

<210> SEQ ID NO 51
<211> LENGTH: 21
<212> TYPE: DNA
<213> ORGANISM: Homo sapiens
<220> FEATURE:
<221> NAME/KEY: misc_feature
<223> OTHER INFORMATION: Sense primer for CXCL11

<400> SEQUENCE: 51
aggacgctgt ctttgcatag g                                               21

<210> SEQ ID NO 52
<211> LENGTH: 25
```

```
<212> TYPE: DNA
<213> ORGANISM: Homo sapiens
<220> FEATURE:
<221> NAME/KEY: misc_feature
<223> OTHER INFORMATION: Antisense primer for CXCL11

<400> SEQUENCE: 52
gcatcgttgt cctttatttt ctttc                                         25

<210> SEQ ID NO 53
<211> LENGTH: 24
<212> TYPE: DNA
<213> ORGANISM: Homo sapiens
<220> FEATURE:
<221> NAME/KEY: misc_feature
<223> OTHER INFORMATION: Sense primer for IL1B

<400> SEQUENCE: 53
gaagatggaa aagcgatttg tctt                                          24

<210> SEQ ID NO 54
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for IL1B

<400> SEQUENCE: 54
gggcatgttt tctgcttgag a                                             21

<210> SEQ ID NO 55
<211> LENGTH: 27
<212> TYPE: DNA
<213> ORGANISM: Homo sapiens
<220> FEATURE:
<221> NAME/KEY: misc_feature
<223> OTHER INFORMATION: Sense primer for IL2

<400> SEQUENCE: 55
gaactaaagg gatctgaaac aacattc                                       27

<210> SEQ ID NO 56
<211> LENGTH: 24
<212> TYPE: DNA
<213> ORGANISM: Homo sapiens
<220> FEATURE:
<221> NAME/KEY: misc_feature
<223> OTHER INFORMATION: Antisense primer for IL2

<400> SEQUENCE: 56
tgttgagatg atgctttgac aaaa                                          24

<210> SEQ ID NO 57
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for IL4

<400> SEQUENCE: 57
cacaggcaca agcagctgat                                               20

<210> SEQ ID NO 58
<211> LENGTH: 23
<212> TYPE: DNA
```

<213> ORGANISM: Homo sapiens
<220> FEATURE:
<221> NAME/KEY: misc_feature
<223> OTHER INFORMATION: Antisense primer for IL4

<400> SEQUENCE: 58
ccttcacagg acaggaattc aag         23

<210> SEQ ID NO 59
<211> LENGTH: 27
<212> TYPE: DNA
<213> ORGANISM: Homo sapiens
<220> FEATURE:
<221> NAME/KEY: misc_feature
<223> OTHER INFORMATION: Sense primer for IL8

<400> SEQUENCE: 59
tgctaaagaa cttagatgtc agtgcat         27

<210> SEQ ID NO 60
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for IL8

<400> SEQUENCE: 60
tggtccactc tcaatcactc tca         23

<210> SEQ ID NO 61
<211> LENGTH: 24
<212> TYPE: DNA
<213> ORGANISM: Homo sapiens
<220> FEATURE:
<221> NAME/KEY: misc_feature
<223> OTHER INFORMATION: Sense primer for IL10

<400> SEQUENCE: 61
gccatgagtg agtttgacat cttc         24

<210> SEQ ID NO 62
<211> LENGTH: 29
<212> TYPE: DNA
<213> ORGANISM: Homo sapiens
<220> FEATURE:
<221> NAME/KEY: misc_feature
<223> OTHER INFORMATION: Antisense primer for IL10

<400> SEQUENCE: 62
gattttggag acctctaatt tatgtccta         29

<210> SEQ ID NO 63
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for IL12A

<400> SEQUENCE: 63
gcaggccctg aatttcaaca         20

<210> SEQ ID NO 64
<211> LENGTH: 29
<212> TYPE: DNA
<213> ORGANISM: Homo sapiens

```
<220> FEATURE:
<221> NAME/KEY: misc_feature
<223> OTHER INFORMATION: Antisense primer for IL12A

<400> SEQUENCE: 64
gaagtatgca gagcttgatt ttagttttta                                    29

<210> SEQ ID NO 65
<211> LENGTH: 21
<212> TYPE: DNA
<213> ORGANISM: Homo sapiens
<220> FEATURE:
<221> NAME/KEY: misc_feature
<223> OTHER INFORMATION: Sense primer for IL17

<400> SEQUENCE: 65
catgaactct gtccccatcc a                                             21

<210> SEQ ID NO 66
<211> LENGTH: 18
<212> TYPE: DNA
<213> ORGANISM: Homo sapiens
<220> FEATURE:
<221> NAME/KEY: misc_feature
<223> OTHER INFORMATION: Antisense primer for IL17

<400> SEQUENCE: 66
tccagccgga aggagttg                                                 18

<210> SEQ ID NO 67
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for IL23

<400> SEQUENCE: 67
cagcaaccct gagtccctaa ag                                            22

<210> SEQ ID NO 68
<211> LENGTH: 18
<212> TYPE: DNA
<213> ORGANISM: Homo sapiens
<220> FEATURE:
<221> NAME/KEY: misc_feature
<223> OTHER INFORMATION: Antisense primer for IL23

<400> SEQUENCE: 68
ttgctgggcc atggagat                                                 18

<210> SEQ ID NO 69
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for FoxP3

<400> SEQUENCE: 69
cacctacgcc acgctcatc                                                19

<210> SEQ ID NO 70
<211> LENGTH: 20
<212> TYPE: DNA
<213> ORGANISM: Homo sapiens
<220> FEATURE:
```

```
<221> NAME/KEY: misc_feature
<223> OTHER INFORMATION: Antisense primer for FoxP3

<400> SEQUENCE: 70
aaggcaaaca tgcgtgtgaa                                               20

<210> SEQ ID NO 71
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for CD25

<400> SEQUENCE: 71
cagaagtcat gaagcccaag tg                                            22

<210> SEQ ID NO 72
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for CD25

<400> SEQUENCE: 72
ggcaagcaca acggatgtct                                               20

<210> SEQ ID NO 73
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for CTLA4

<400> SEQUENCE: 73
catgcctcct cttcttcctt ga                                            22

<210> SEQ ID NO 74
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for CTLA4

<400> SEQUENCE: 74
ggagggtgcc accatgacta                                               20

<210> SEQ ID NO 75
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for Granzyme B

<400> SEQUENCE: 75
gcggtggctt cctgatacaa                                               20

<210> SEQ ID NO 76
<211> LENGTH: 23
<212> TYPE: DNA
<213> ORGANISM: Homo sapiens
<220> FEATURE:
<221> NAME/KEY: misc_feature
```

<223> OTHER INFORMATION: Antisense primer for Granzyme B

<400> SEQUENCE: 76
ccaaggtgac atttatggag ctt                                    23

<210> SEQ ID NO 77
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for CD8A

<400> SEQUENCE: 77
ccgagagaac gagggctact att                                    23

<210> SEQ ID NO 78
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for CD8A

<400> SEQUENCE: 78
gcacgaagtg gctgaagtac at                                     22

<210> SEQ ID NO 79
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for C16

<400> SEQUENCE: 79
gtttggcagt gtcaaccatc tc                                     22

<210> SEQ ID NO 80
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for CD16

<400> SEQUENCE: 80
aaaaggagta ccatcaccaa gca                                    23

<210> SEQ ID NO 81
<211> LENGTH: 18
<212> TYPE: DNA
<213> ORGANISM: Homo sapiens
<220> FEATURE:
<221> NAME/KEY: misc_feature
<223> OTHER INFORMATION: Sense primer for CD32A

<400> SEQUENCE: 81
gctgacggcg gctacatg                                          18

<210> SEQ ID NO 82
<211> LENGTH: 29
<212> TYPE: DNA
<213> ORGANISM: Homo sapiens
<220> FEATURE:
<221> NAME/KEY: misc_feature
<223> OTHER INFORMATION: Antisense primer for CD32A

```
<400> SEQUENCE: 82
gaggaagagt caggtagatg tttttatca                                          29

<210> SEQ ID NO 83
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for CD64

<400> SEQUENCE: 83
ctggcagtgg gaataatgtt ttt                                                23

<210> SEQ ID NO 84
<211> LENGTH: 29
<212> TYPE: DNA
<213> ORGANISM: Homo sapiens
<220> FEATURE:
<221> NAME/KEY: misc_feature
<223> OTHER INFORMATION: Antisense primer for  CD64

<400> SEQUENCE: 84
cactttttct ttcttttcag ttctttgcg                                          29

<210> SEQ ID NO 85
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for IgG Fc

<400> SEQUENCE: 85
cagccggaga acaactacaa gac                                                23

<210> SEQ ID NO 86
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for IgG Fc

<400> SEQUENCE: 86
gctgccacct gctcttgtc                                                     19

<210> SEQ ID NO 87
<211> LENGTH: 26
<212> TYPE: DNA
<213> ORGANISM: Homo sapiens
<220> FEATURE:
<221> NAME/KEY: misc_feature
<223> OTHER INFORMATION: Sense primer for Arginase

<400> SEQUENCE: 87
agacaccaga agaagtaact cgaaca                                             26

<210> SEQ ID NO 88
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for ARG
```

<400> SEQUENCE: 88
tcccgagcaa gtccgaaac                                                19

<210> SEQ ID NO 89
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for MPO

<400> SEQUENCE: 89
actgcctggg ttccaatcc                                                19

<210> SEQ ID NO 90
<211> LENGTH: 25
<212> TYPE: DNA
<213> ORGANISM: Homo sapiens
<220> FEATURE:
<221> NAME/KEY: misc_feature
<223> OTHER INFORMATION: Antisense primer for MPO

<400> SEQUENCE: 90
tgtttaagga gggtaatttg ctcaa                                         25

<210> SEQ ID NO 91
<211> LENGTH: 25
<212> TYPE: DNA
<213> ORGANISM: Homo sapiens
<220> FEATURE:
<221> NAME/KEY: misc_feature
<223> OTHER INFORMATION: Sense primer for TLR2

<400> SEQUENCE: 91
gaagagtgag tggtgcaagt atgaa                                         25

<210> SEQ ID NO 92
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for TLR2

<400> SEQUENCE: 92
atggcagcat cattgttctc atc                                           23

<210> SEQ ID NO 93
<211> LENGTH: 21
<212> TYPE: DNA
<213> ORGANISM: Homo sapiens
<220> FEATURE:
<221> NAME/KEY: misc_feature
<223> OTHER INFORMATION: Sense primer for TLR4

<400> SEQUENCE: 93
gattgctcag acctggcagt t                                             21

<210> SEQ ID NO 94
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for TLR4

<400> SEQUENCE: 94
tgtcctccca ctccaggtaa gt                                            22

<210> SEQ ID NO 95
<211> LENGTH: 18
<212> TYPE: DNA
<213> ORGANISM: Homo sapiens
<220> FEATURE:
<221> NAME/KEY: misc_feature
<223> OTHER INFORMATION: Sense primer for GM-CSF

<400> SEQUENCE: 95
ggccccttga ccatgatg                                                 18

<210> SEQ ID NO 96
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for GM-CSF

<400> SEQUENCE: 96
tctgggttgc acaggaagtt t                                             21

<210> SEQ ID NO 97
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for IFN-gamma

<400> SEQUENCE: 97
ggagaccatc aaggaagaca tga                                           23

<210> SEQ ID NO 98
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for IFN-gamma

<400> SEQUENCE: 98
gctttgcgtt ggacattcaa                                               20

<210> SEQ ID NO 99
<211> LENGTH: 24
<212> TYPE: DNA
<213> ORGANISM: Homo sapiens
<220> FEATURE:
<221> NAME/KEY: misc_feature
<223> OTHER INFORMATION: Sense primer for TGF-beta

<400> SEQUENCE: 99
ctgctgaggc tcaagttaaa agtg                                          24

<210> SEQ ID NO 100
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for TGF-beta

<400> SEQUENCE: 100
tgaggtatcg ccaggaattg t                                              21

<210> SEQ ID NO 101
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for CD4

<400> SEQUENCE: 101
aaatgccaca cggctctca                                                 19

<210> SEQ ID NO 102
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for CD4

<400> SEQUENCE: 102
gggtgctgtg cttctgtgaa c                                              21

<210> SEQ ID NO 103
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for STAT 1

<400> SEQUENCE: 103
gtggaaagac agccctgcat                                                20

<210> SEQ ID NO 104
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for STAT 1

<400> SEQUENCE: 104
actggacccc tgtcttcaag ac                                             22

<210> SEQ ID NO 105
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for STAT 3

<400> SEQUENCE: 105
gccagagagc caggagcat                                                 19

<210> SEQ ID NO 106
<211> LENGTH: 26
<212> TYPE: DNA
<213> ORGANISM: Homo sapiens
<220> FEATURE:
<221> NAME/KEY: misc_feature
<223> OTHER INFORMATION: Antisense primer for STAT 3

<400> SEQUENCE: 106
ggtgtcacac agataaactt ggtctt                                         26

```
<210> SEQ ID NO 107
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for STAT 4

<400> SEQUENCE: 107
catttggtac aacgtgtcaa cca                                           23

<210> SEQ ID NO 108
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for STAT 4

<400> SEQUENCE: 108
tgtggcaggt ggaggattat ta                                            22

<210> SEQ ID NO 109
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for VEGF

<400> SEQUENCE: 109
cgcagctact gccatccaat                                               20

<210> SEQ ID NO 110
<211> LENGTH: 24
<212> TYPE: DNA
<213> ORGANISM: Homo sapiens
<220> FEATURE:
<221> NAME/KEY: misc_feature
<223> OTHER INFORMATION: Antisense primer for VEGF

<400> SEQUENCE: 110
tggcttgaag atgtactcga tctc                                          24

<210> SEQ ID NO 111
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for POMC

<400> SEQUENCE: 111
acgagggccc ctacaggat                                                19

<210> SEQ ID NO 112
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for POMC

<400> SEQUENCE: 112
tgatgatggc gttttttgaac a                                            21
```

<210> SEQ ID NO 113
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for GBP

<400> SEQUENCE: 113
agaagtgaag gcgggaattt att                                              23

<210> SEQ ID NO 114
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for GBP

<400> SEQUENCE: 114
atccccttcc tcggttcct                                                   19

<210> SEQ ID NO 115
<211> LENGTH: 26
<212> TYPE: DNA
<213> ORGANISM: Homo sapiens
<220> FEATURE:
<221> NAME/KEY: misc_feature
<223> OTHER INFORMATION: Sense primer for XAF1

<400> SEQUENCE: 115
cctagaggag ataaagcagc ctatga                                           26

<210> SEQ ID NO 116
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for XAF1

<400> SEQUENCE: 116
aagctaacca ccggcatttc t                                                21

<210> SEQ ID NO 117
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for AIM2

<400> SEQUENCE: 117
ggtgaaaccc cgaagatcaa                                                  20

<210> SEQ ID NO 118
<211> LENGTH: 25
<212> TYPE: DNA
<213> ORGANISM: Homo sapiens
<220> FEATURE:
<221> NAME/KEY: misc_feature
<223> OTHER INFORMATION: Antisense primer for AIM2

<400> SEQUENCE: 118
ctggactaca aacaaaccat tcaca                                            25

```
<210> SEQ ID NO 119
<211> LENGTH: 19
<212> TYPE: DNA
<213> ORGANISM: Homo sapiens
<220> FEATURE:
<221> NAME/KEY: misc_feature
<223> OTHER INFORMATION: Sense primer for SHP2

<400> SEQUENCE: 119
tccagatggt gcggtctca                                               19

<210> SEQ ID NO 120
<211> LENGTH: 25
<212> TYPE: DNA
<213> ORGANISM: Homo sapiens
<220> FEATURE:
<221> NAME/KEY: misc_feature
<223> OTHER INFORMATION: Antisense primer for SHP2

<400> SEQUENCE: 120
cctgcgctgt agtgtttcaa tataa                                        25

<210> SEQ ID NO 121
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for SOCS1

<400> SEQUENCE: 121
ggaactgctt tttcgcccTT agc                                          23

<210> SEQ ID NO 122
<211> LENGTH: 21
<212> TYPE: DNA
<213> ORGANISM: Homo sapiens
<220> FEATURE:
<221> NAME/KEY: misc_feature
<223> OTHER INFORMATION: Antisense primer for SOCS1

<400> SEQUENCE: 122
ctgaaagtgc acgcggatgc t                                            21

<210> SEQ ID NO 123
<211> LENGTH: 25
<212> TYPE: DNA
<213> ORGANISM: Homo sapiens
<220> FEATURE:
<221> NAME/KEY: misc_feature
<223> OTHER INFORMATION: Sense primer for SLP76

<400> SEQUENCE: 123
ccgttatcag aaggaaagtc aagtt                                        25

<210> SEQ ID NO 124
<211> LENGTH: 28
<212> TYPE: DNA
<213> ORGANISM: Homo sapiens
<220> FEATURE:
<221> NAME/KEY: misc_feature
<223> OTHER INFORMATION: Antisense primer for SLP76

<400> SEQUENCE: 124
atatctgaca cagacagaaa gtcctctt                                     28

<210> SEQ ID NO 125
```

```
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for G1P2

<400> SEQUENCE: 125
caaatgcgac gaacctctga                                               20

<210> SEQ ID NO 126
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for G1P2

<400> SEQUENCE: 126
ccgctcactt gctgcttca                                                19

<210> SEQ ID NO 127
<211> LENGTH: 30
<212> TYPE: DNA
<213> ORGANISM: Homo sapiens
<220> FEATURE:
<221> NAME/KEY: misc_feature
<223> OTHER INFORMATION: Sense primer for BST2

<400> SEQUENCE: 127
gagatcacta cattaaacca taagcttcag                                    30

<210> SEQ ID NO 128
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for BST2

<400> SEQUENCE: 128
tctcacgctt aagacctggt ttt                                           23

<210> SEQ ID NO 129
<211> LENGTH: 23
<212> TYPE: DNA
<213> ORGANISM: Homo sapiens
<220> FEATURE:
<221> NAME/KEY: misc_feature
<223> OTHER INFORMATION: Sense primer for IRF7

<400> SEQUENCE: 129
tccccacgct ataccatcta cct                                           23

<210> SEQ ID NO 130
<211> LENGTH: 19
<212> TYPE: DNA
<213> ORGANISM: Homo sapiens
<220> FEATURE:
<221> NAME/KEY: misc_feature
<223> OTHER INFORMATION: Antisense primer for IRF7

<400> SEQUENCE: 130
acagccaggg ttccagctt                                                19

<210> SEQ ID NO 131
<211> LENGTH: 20
```

```
<212> TYPE: DNA
<213> ORGANISM: Homo sapiens
<220> FEATURE:
<221> NAME/KEY: misc_feature
<223> OTHER INFORMATION: Sense primer for LCK

<400> SEQUENCE: 131
ttaagtggac agcgccagaa                                              20

<210> SEQ ID NO 132
<211> LENGTH: 23
<212> TYPE: DNA
<213> ORGANISM: Homo sapiens
<220> FEATURE:
<221> NAME/KEY: misc_feature
<223> OTHER INFORMATION: Antisense primer for LCK

<400> SEQUENCE: 132
cccaaaagac cacacatctg act                                          23
```